United States Patent
Lee et al.

(10) Patent No.: US 8,961,571 B2
(45) Date of Patent: Feb. 24, 2015

(54) METHOD AND APPARATUS FOR SPINAL FACET JOINT FUSION USING IRREGULARLY SHAPED CORTICAL BONE IMPLANTS

(76) Inventors: David Lee, Hattiesburg, MS (US); James Payne, Jr., Vancleave, MS (US)

( * ) Notice: Subject to any disclaimer, the term of this patent is extended or adjusted under 35 U.S.C. 154(b) by 688 days.

(21) Appl. No.: 12/273,790

(22) Filed: Nov. 19, 2008

(65) Prior Publication Data
US 2009/0131986 A1 May 21, 2009

Related U.S. Application Data

(60) Provisional application No. 60/988,911, filed on Nov. 19, 2007.

(51) Int. Cl.
*A61B 17/88* (2006.01)
*A61B 17/70* (2006.01)
(Continued)

(52) U.S. Cl.
CPC ......... *A61B 17/7064* (2013.01); *A61B 17/1604* (2013.01); *A61B 17/1671* (2013.01); *A61F 2/4405* (2013.01); *A61F 2/4601* (2013.01); *A61F 2/4611* (2013.01); *A61F 2/4657* (2013.01); *A61B 17/846* (2013.01); *A61B 2017/90* (2013.01); *A61F 2/28* (2013.01); *A61F 2/4455* (2013.01); *A61F 2002/30112* (2013.01); *A61F 2002/3013* (2013.01); *A61F 2002/30163* (2013.01); *A61F 2002/30171* (2013.01); *A61F 2002/30179* (2013.01); *A61F 2002/30571* (2013.01); *A61F 2002/30576* (2013.01); *A61F 2002/30601* (2013.01); *A61F 2002/30617* (2013.01); *A61F 2002/30881* (2013.01); *A61F 2002/30883* (2013.01); *A61F 2002/4627* (2013.01); *A61F 2002/4628* (2013.01); *A61F 2002/4668* (2013.01); *A61F 2002/4681* (2013.01); *A61F 2230/0004* (2013.01); *A61F 2230/001* (2013.01); *A61F 2230/0028* (2013.01); *A61F 2230/005* (2013.01); *A61F 2230/0058* (2013.01); *A61F 2250/0097* (2013.01);
(Continued)

(58) Field of Classification Search
USPC .................................. 606/60, 246, 247, 279
See application file for complete search history.

(56) References Cited

U.S. PATENT DOCUMENTS 4,501,269 A  2/1985 Bagby
5,364,400 A  11/1994 Rego, Jr. et al.
(Continued)

FOREIGN PATENT DOCUMENTS

CA  2586352  6/2006
EP  1764066  3/2007
(Continued)

OTHER PUBLICATIONS

Jose M. Otero Vich, M.D., "Anterior cervical interobdy fusion with threaded cylindrical bone", J. Neurosurg, vol. 63, pp. 750-753, 1985.
(Continued)

*Primary Examiner* — Ellen C Hammond
(74) *Attorney, Agent, or Firm* — Garvey, Smith, Nehrbass & North, L.L.C.; Brett A. North

(57) ABSTRACT

A method and apparatus for spinal fusion at the facet joint using an irregularly shaped implant where the orientation of the implant can be preselected before implantation.

9 Claims, 28 Drawing Sheets

(51) Int. Cl.

| | | |
|---|---|---|
| *A61B 17/16* | (2006.01) | |
| *A61F 2/44* | (2006.01) | |
| *A61F 2/46* | (2006.01) | |
| A61B 17/84 | (2006.01) | |
| A61B 17/90 | (2006.01) | |
| A61F 2/28 | (2006.01) | |
| A61F 2/30 | (2006.01) | |

(52) U.S. Cl.
CPC .............. *A61F2002/4687* (2013.01); *A61F 2310/00359* (2013.01)
USPC ........................................ 606/279; 606/247

(56) References Cited

U.S. PATENT DOCUMENTS

| | | | |
|---|---|---|---|
| 5,383,878 A | 1/1995 | Roger et al. | |
| 5,397,362 A | 3/1995 | Noda | |
| 5,470,334 A | 11/1995 | Ross et al. | |
| 5,507,813 A | 4/1996 | Dowd et al. | |
| 5,709,683 A | 1/1998 | Bagby | |
| 6,042,578 A | 3/2000 | Dinh et al. | |
| 6,045,554 A | 4/2000 | Grooms et al. | |
| 6,210,412 B1 | 4/2001 | Michelson | |
| 6,368,322 B1 | 4/2002 | Luks et al. | |
| 6,485,518 B1 | 11/2002 | Cornwall et al. | |
| 6,902,578 B1 | 6/2005 | Anderson et al. | |
| 6,923,810 B1 | 8/2005 | Michelson | |
| 7,094,239 B1 | 8/2006 | Michelson | |
| 7,575,600 B2 * | 8/2009 | Zucherman et al. | 623/17.15 |
| 2002/0052605 A1 | 5/2002 | Grooms et al. | |
| 2004/0215344 A1 | 10/2004 | Hochschuler et al. | |
| 2005/0015150 A1 | 1/2005 | Lee | |
| 2005/0131548 A1 | 6/2005 | Boyer, II et al. | |
| 2005/0149192 A1 | 7/2005 | Zucherman et al. | |
| 2006/0111779 A1 | 5/2006 | Petersen | |
| 2006/0111780 A1 | 5/2006 | Petersen | |
| 2006/0111781 A1 | 5/2006 | Petersen | |
| 2006/0111782 A1 * | 5/2006 | Petersen | 623/17.11 |
| 2006/0111786 A1 | 5/2006 | Petersen | |
| 2006/0247790 A1 * | 11/2006 | McKay | 623/23.44 |
| 2007/0055246 A1 | 3/2007 | Zucherman et al. | |
| 2007/0185492 A1 | 8/2007 | Chervitz et al. | |
| 2007/0250166 A1 | 10/2007 | McKay | |
| 2009/0036927 A1 * | 2/2009 | Vestgaarden | 606/247 |

FOREIGN PATENT DOCUMENTS

| | | |
|---|---|---|
| WO | WO 00/66011 | 11/2000 |
| WO | WO 01/72233 | 10/2001 |
| WO | WO 01/80753 A2 | 11/2001 |
| WO | WO 01/80753 A3 | 11/2001 |
| WO | WO 2006/057943 A2 | 6/2006 |
| WO | WO 2006/057943 A3 | 6/2006 |

OTHER PUBLICATIONS

Jose M. Otero Vich, M.D., "Update on the Cloward procedure: new instruments", J. Neurosurg, vol. 81, pp. 716-720, Nov. 1994.

Allan F. Tencer, PhD, David Hampton, BEng, Sharon Eddy, BEng, Biomechanical Properties of Threaded Inserts for Lumbar Interbody Spinal Fusion, Spine, vol. 20, No. 22, pp. 2408-2414, 1995.

Bryan Barnes, M.D., Gerald E. Rodts, M.D., Mark R. McLaughlin, M.D., Regis W. Haid, Jr., M.D., "Threaded cortical bone dowels for lumbar interbody fusion: over 1-year mean follow up in 28 patients", J. Neurosurg: Spine, vol. 95, pp. 1-4, Jul. 2001.

Davi P. Haje; Jose B. Volpon, "Bovine Bone Screws Development: Machining Method and Metrological Study With Profile Projector", ACTA Ortop Bras 14(2)—2006.

Minsurg Biomechanical Innovations, "TruFUSE Facet Fusion Allografts", Frequently Asked Questions, 2006, Orthopedic Development Corporation.

* cited by examiner

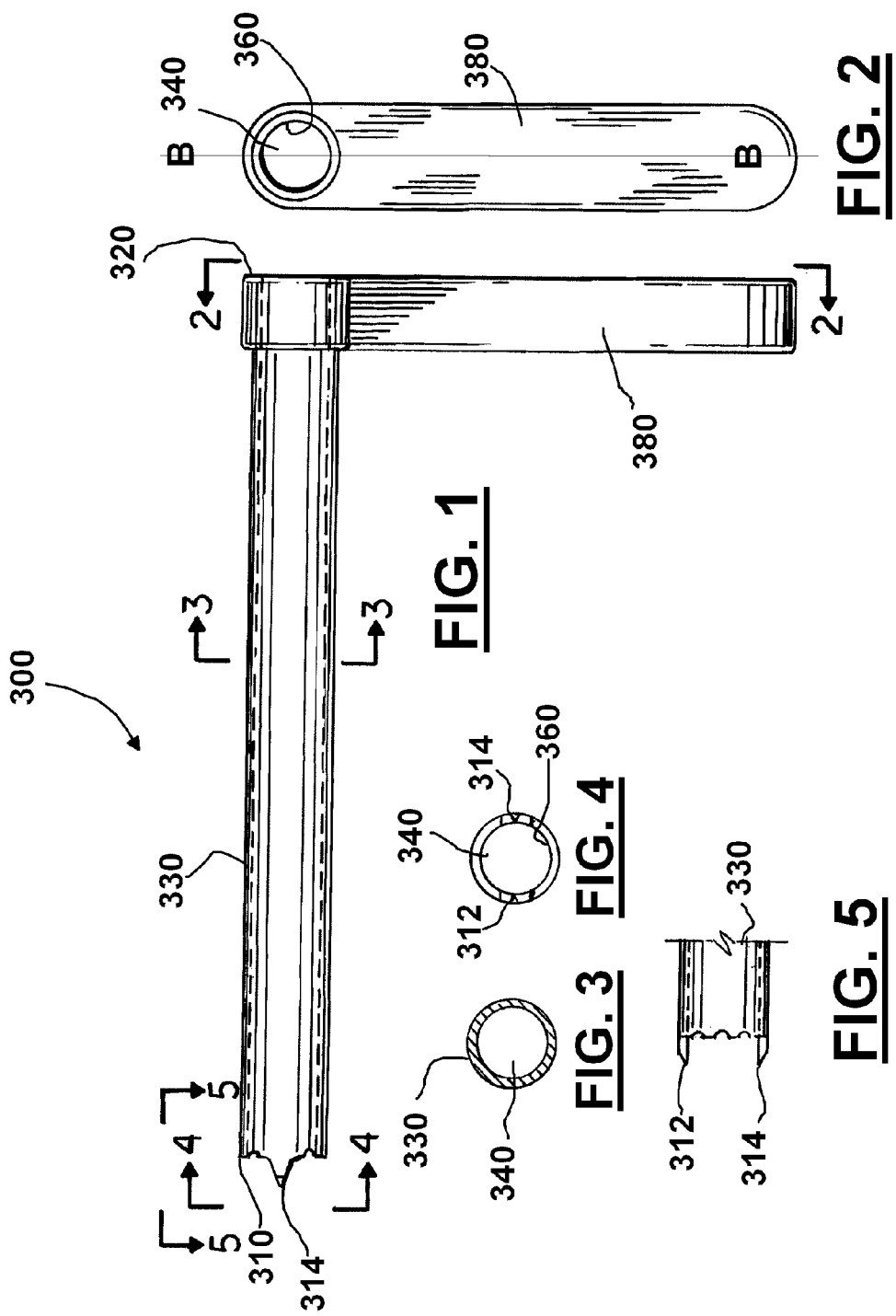

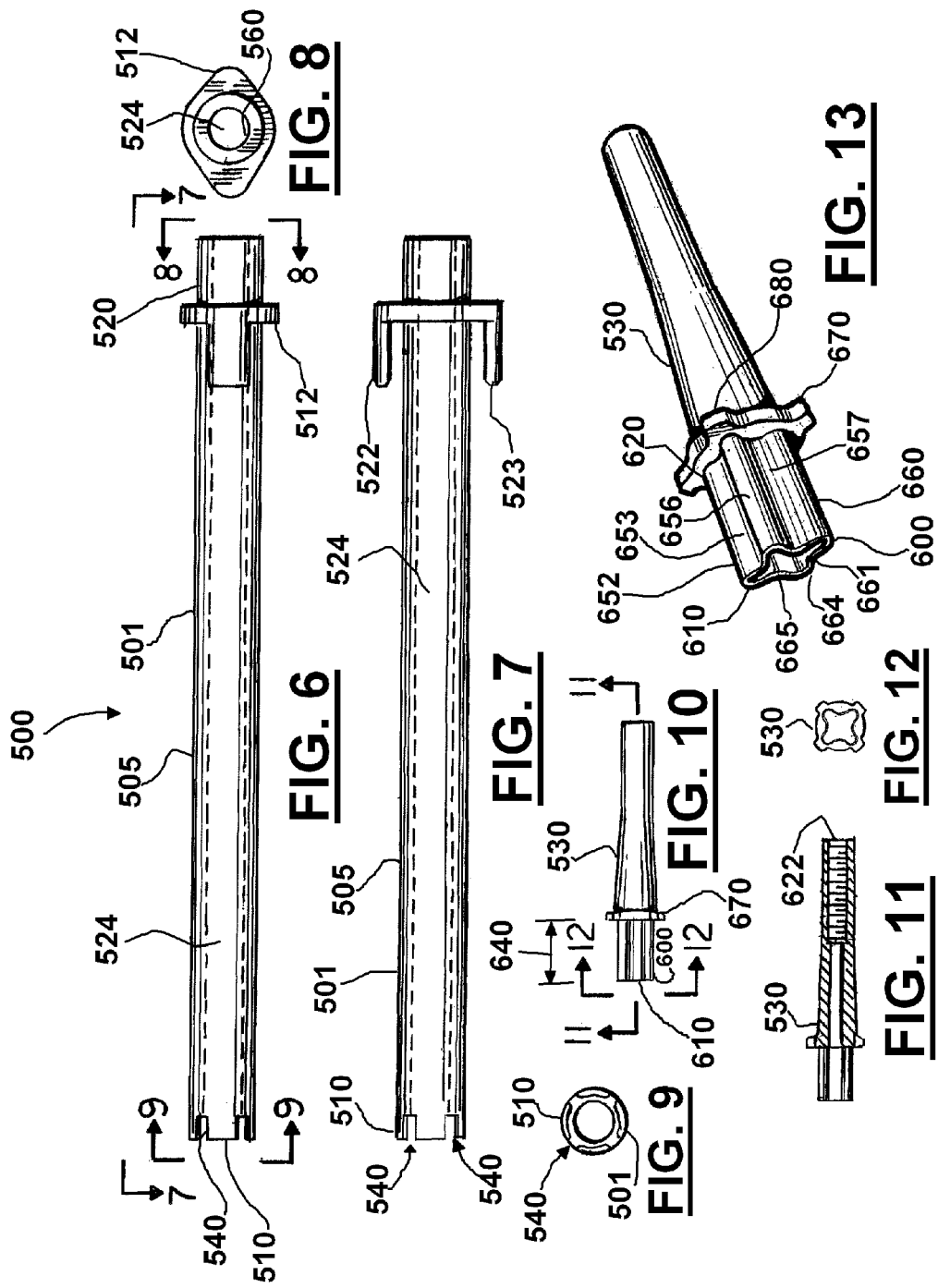

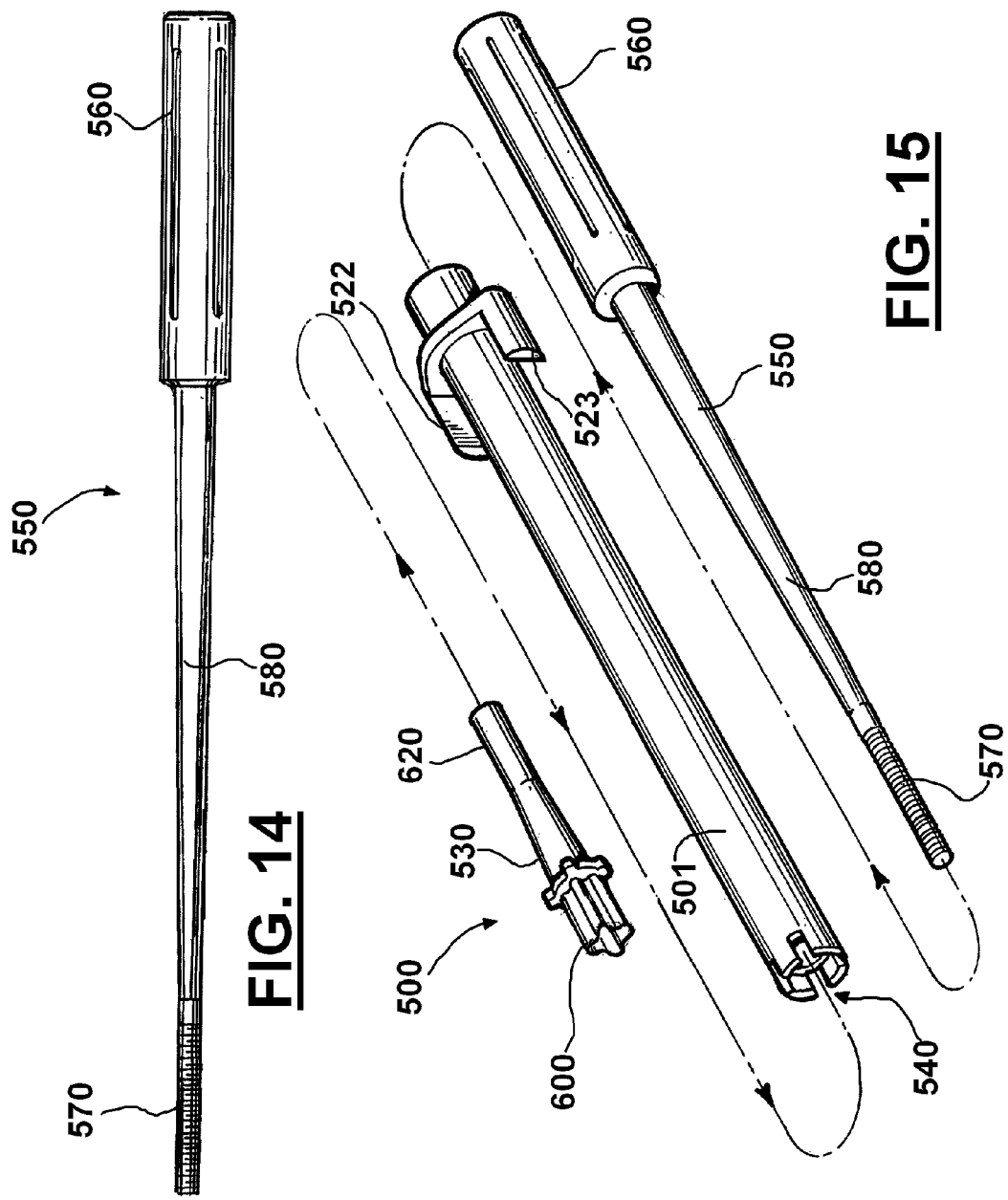

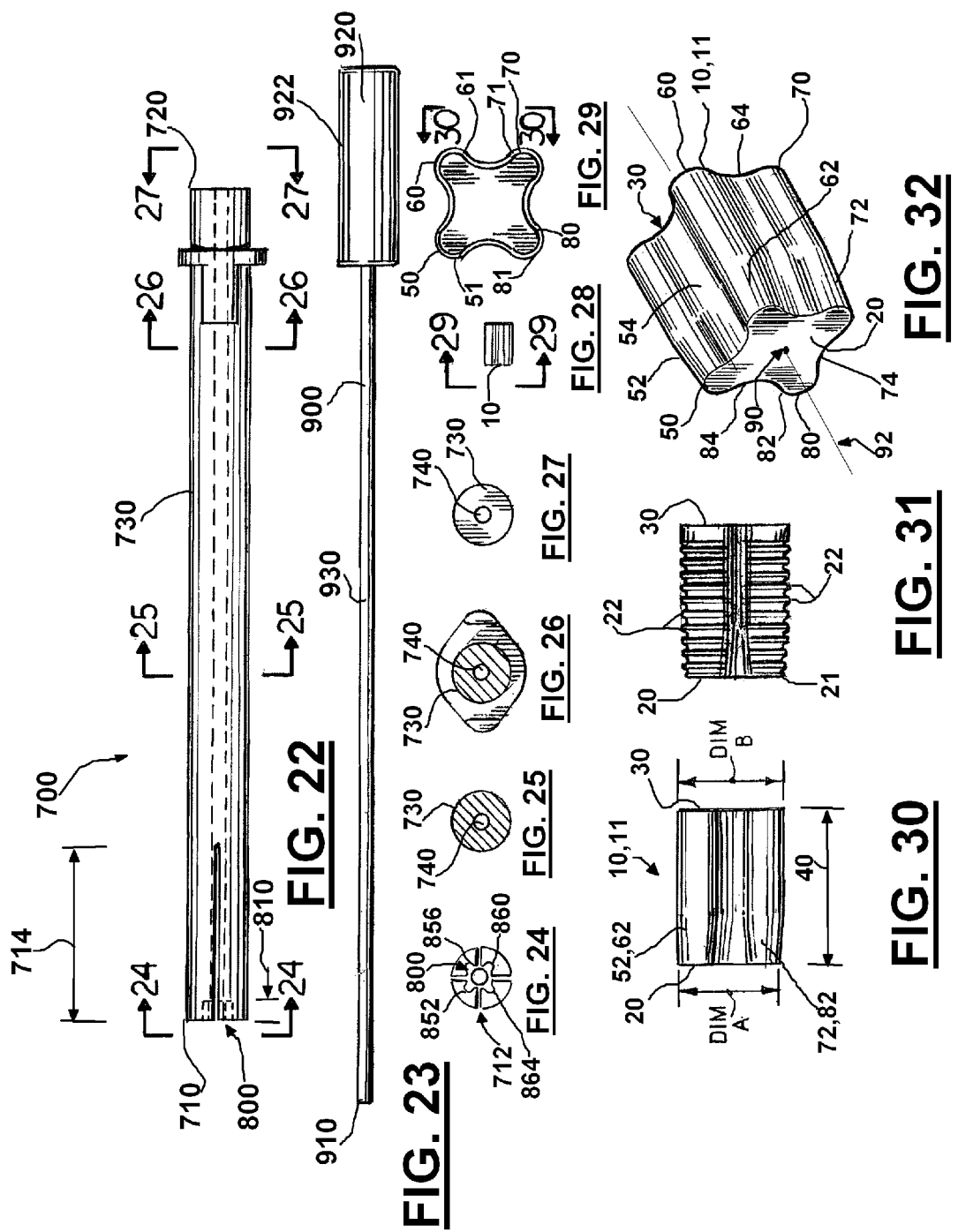

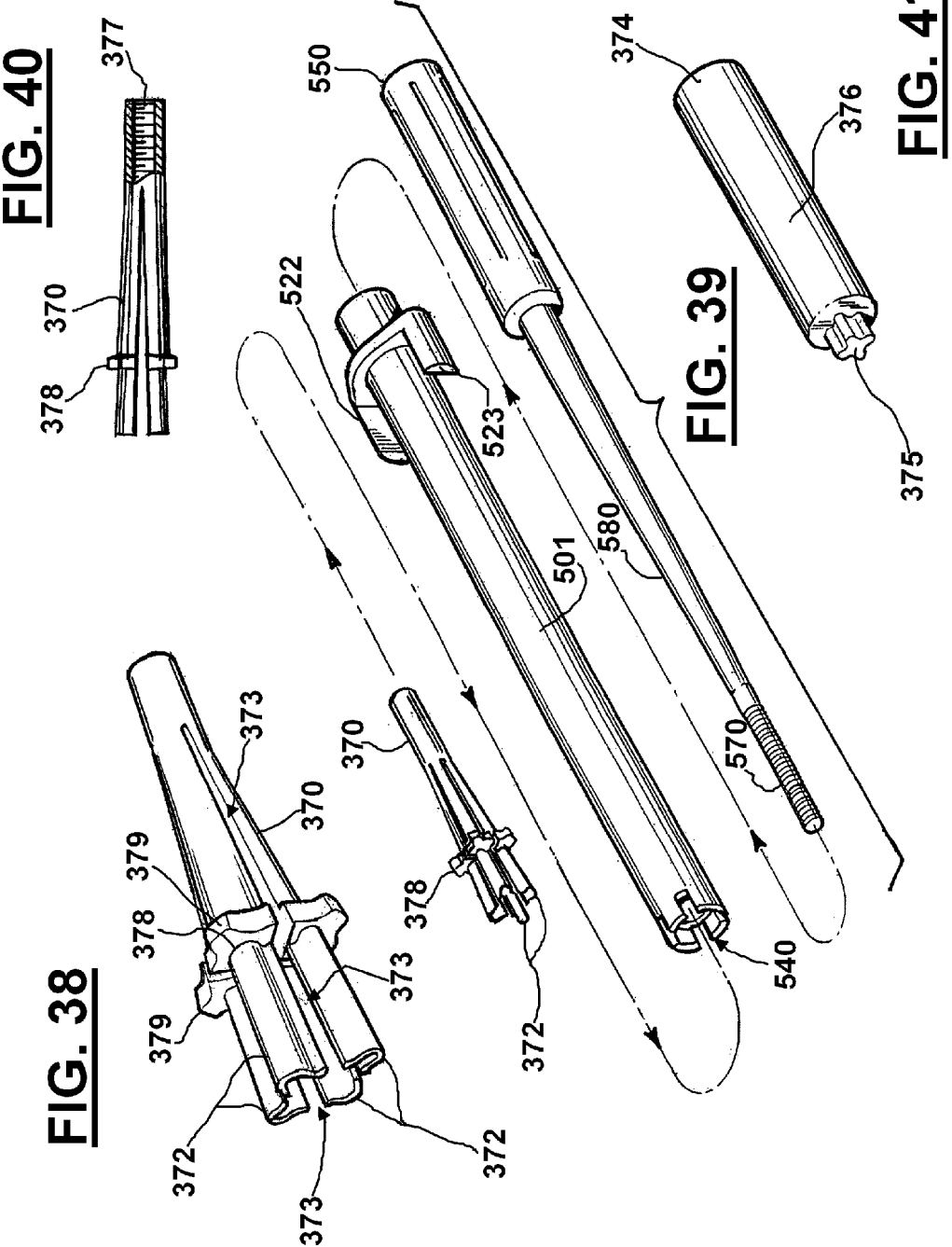

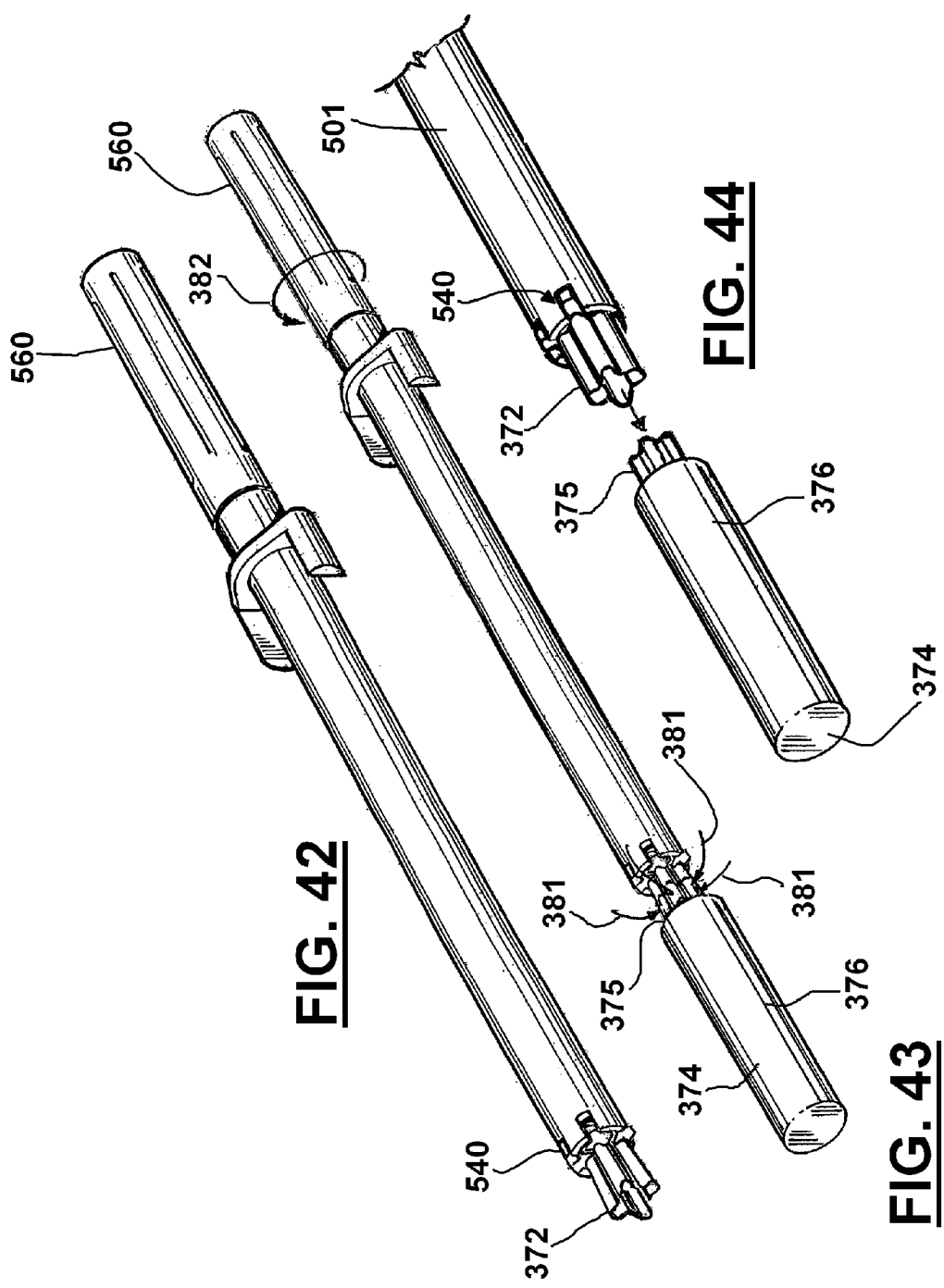

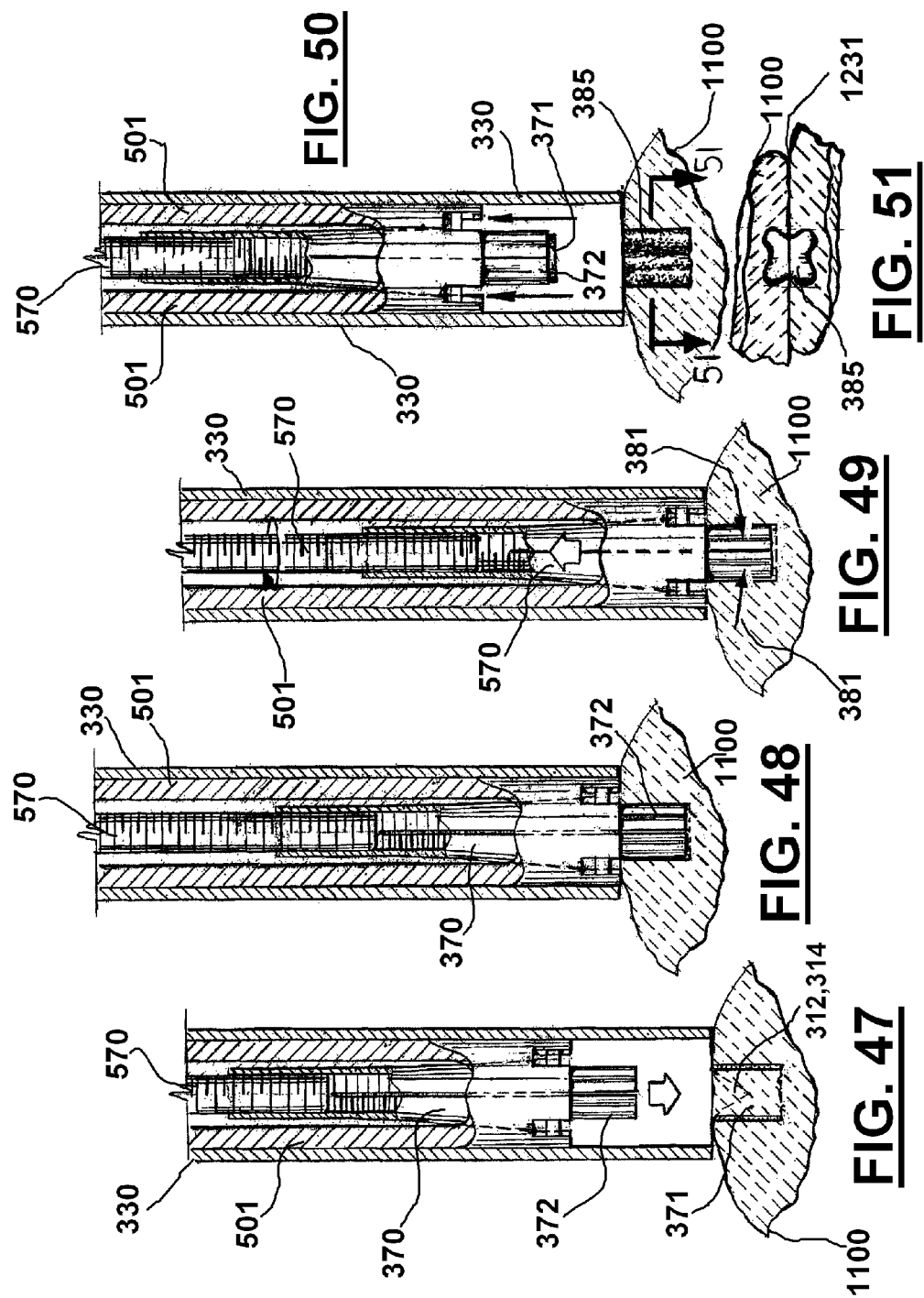

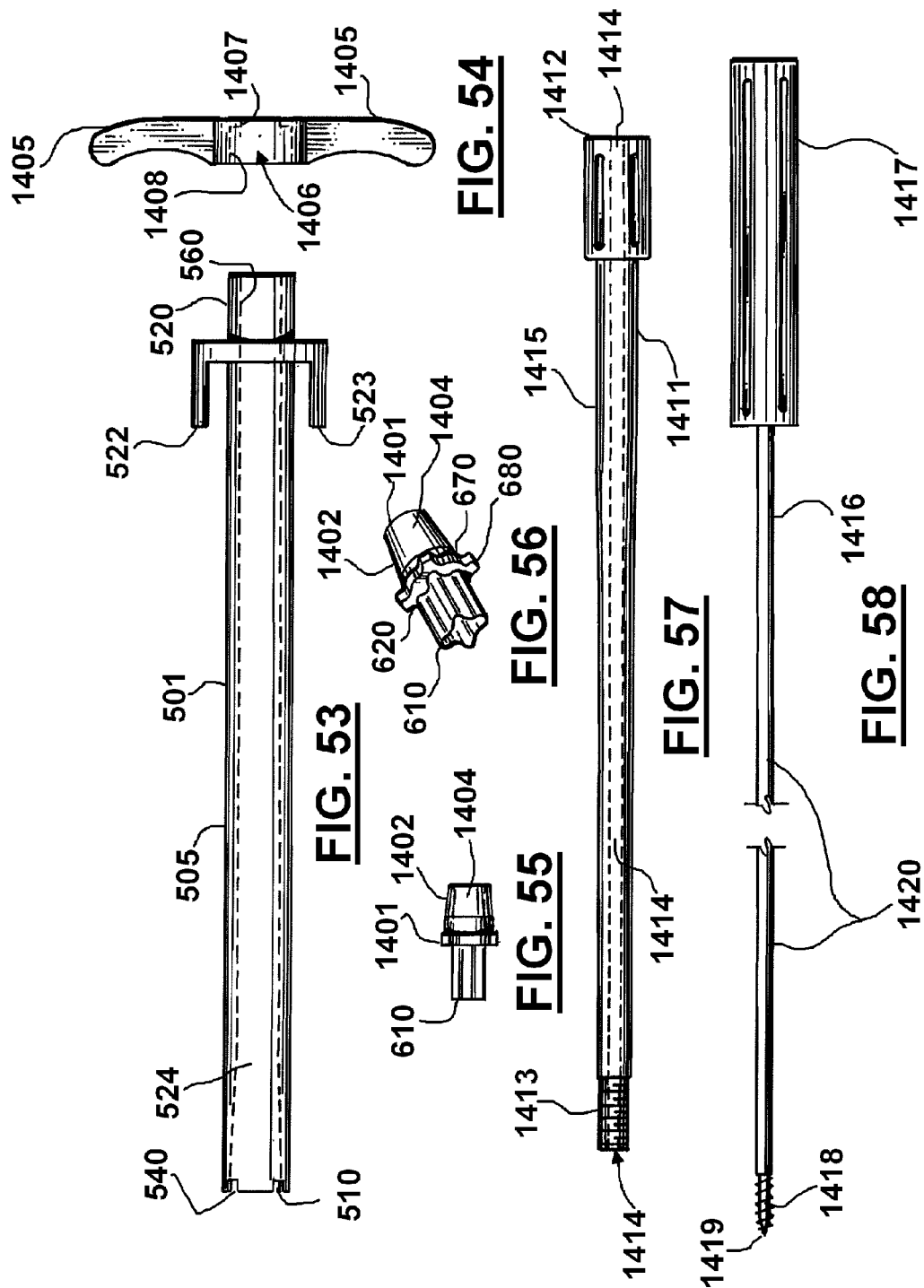

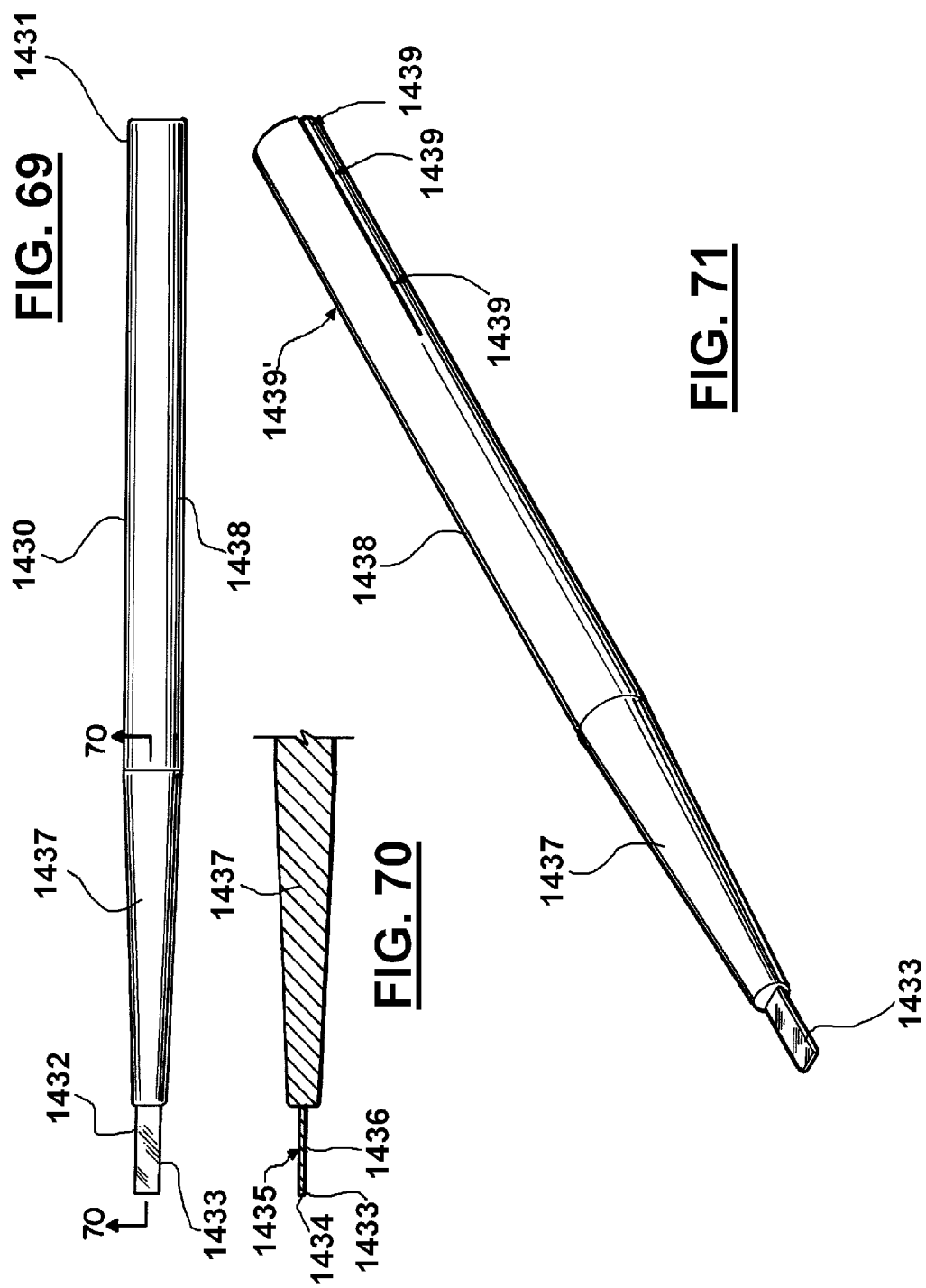

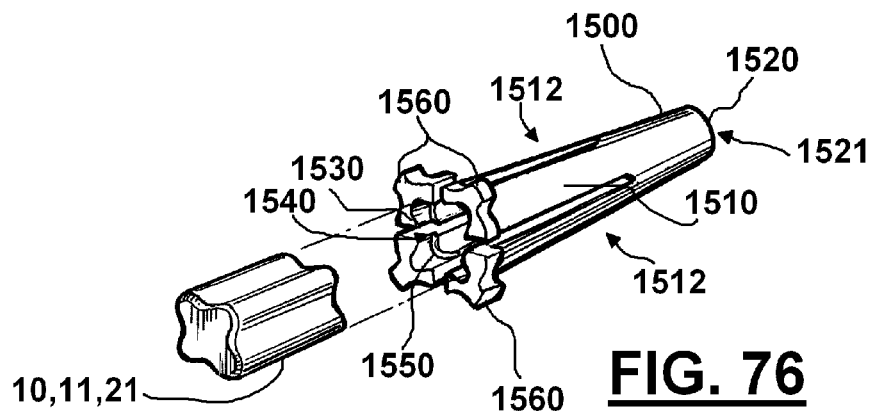
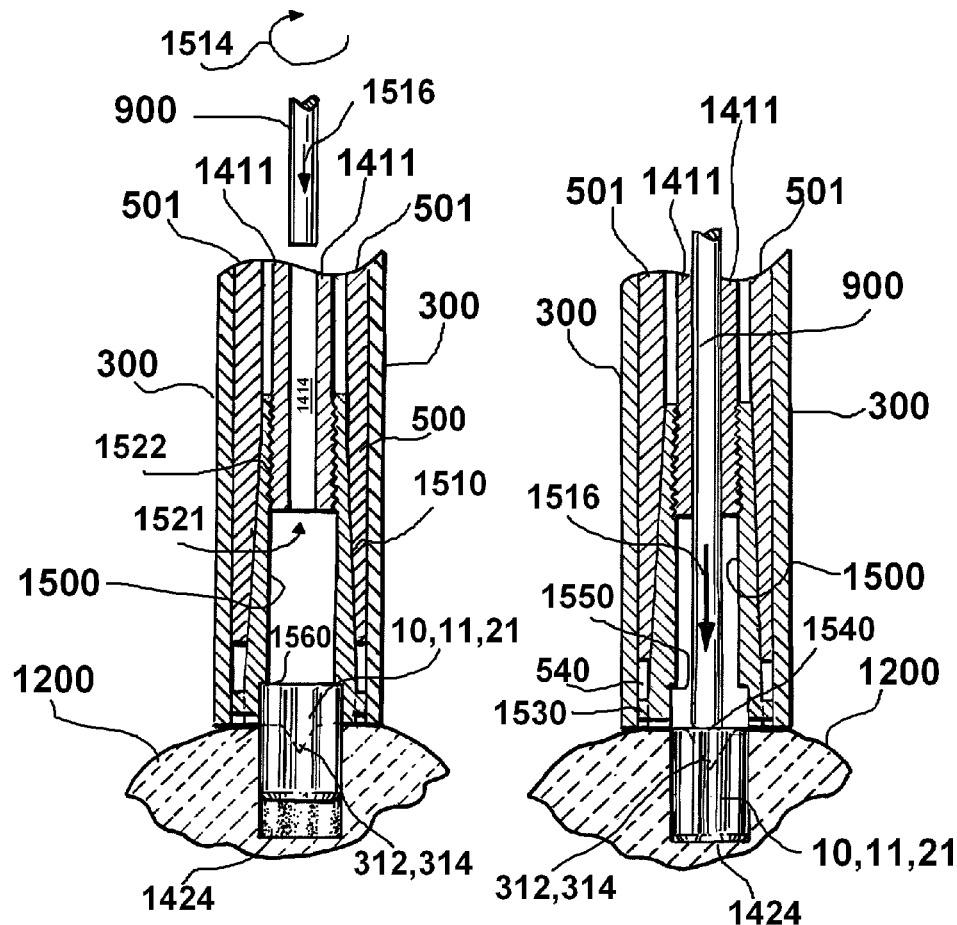
FIG. 76
FIG. 77  FIG. 78

METHOD AND APPARATUS FOR SPINAL FACET JOINT FUSION USING IRREGULARLY SHAPED CORTICAL BONE IMPLANTS

CROSS-REFERENCE TO RELATED APPLICATIONS

Priority of U.S. Provisional Patent Application Ser. No. 60/988,911, filed Nov. 19, 2007, incorporated herein by reference, is hereby claimed.

BACKGROUND

The spine includes a row of 26 bones in the back and allows a person to stand up straight and bend over. The spine also protects a person's spinal cord from being hurt. In people with spinal stenosis, the spine is narrowed in one or more of three parts: (1) the space at the center of the spine; (2) the canals where nerves branch out from the spine; and (3) the space between vertebrae (the bones of the spine). This narrowing puts pressure on the spinal cord and nerves and can cause pain.

Facet joints are small stabilizing joints located between and behind adjacent vertebrae of the spine. Facet joints restrict excessive motion, twisting, or toppling over of the vertebrae relative to one another.

It is believed that facet joint disorders (such as facet joint deterioration and disease) are among the most common of all the recurrent, disabling low back problems that have serious symptoms and disability. In many cases where facet joints are excessively damaged, preventing movement to manage pain is preferred to attempts to repair the joints such as by replacements.

Facet joint fusion can be a stand alone treatment system or a supplement to other fusion systems by fixing facet joints and reducing stress on the primary fusion system compared to when the facet joints are allowed to freely move relative to one another.

It is believed that many conventionally used fusion systems fail prematurely because of mechanical failure of one or more facet joints, and degenerative joint disease.

Treatment of degenerative disc disease, degenerative joint disease, osteoarthritis and other indications of spinal problems typically have included spinal fusion using pedicle and other screw based fixation systems, such as trans-facet compression screws (i.e., perpendicular to the facet plane), and lumbar facet interference screw systems. Facet dowels have also been used, but have been found in many cases to extrude from the insertion location, failing to promote fusion.

Caused by aging, spinal stenosis is most common in men and women over 50 years old. Younger people who were born with a narrow spinal canal or who hurt their spines may also get spinal stenosis. Changes that occur in the spine as people get older are the most common cause of spinal stenosis such as: (a) the bands of tissue that support the spine may get thick and hard; (b) bones and joints may get bigger; and (c) surfaces of the bones may bulge out, which are called bone spurs. In some cases arthritis, a degenerative condition, can cause spinal stenosis. Two forms of arthritis that may affect the spine are: (a) osteoarthritis and (b) rheumatoid arthritis.

Osteoarthritis is the most common form of arthritis and most often occurs in middle-aged and older people. It may involve many joints in the body where it wears away the tough tissue (cartilage) that keeps the joints in place and can cause bone spurs and problems with joints.

Rheumatoid Arthritis affects most people at a younger age than osteoarthritis. It causes the soft tissues of the joints to swell and can affect internal organs and systems. However, it is not a common cause of spinal stenosis but can cause severe damage, especially to joints.

Some people are born with conditions that cause spinal stenosis. For instance, some people are born with a small spinal canal. Others are born with a curved spine (scoliosis). Other causes of spinal stenosis are: tumors of the spine; injuries; Paget's disease (a disease that affects the bones); too much fluoride in the body; and calcium deposits on the ligaments that run along the spine.

In many cases there may be no symptoms of spinal stenosis, or symptoms may appear slowly and get worse over time. Signs of spinal stenosis include: pain in the neck or back; numbness, weakness, cramping, or pain in the arms or legs; pain going down the leg; and foot problems.

One type of spinal stenosis, cauda equine syndrome, is very serious. This type occurs when there is pressure on nerves in the lower back. Symptoms may include: loss of control of the bowel or bladder; problems having sex; and pain, weakness, or loss of feeling in one or both legs.

Because spinal stenosis has many causes and symptoms, treatment may be required from doctors who specialize in certain aspects of the condition. Health care providers can include: rheumatologists (doctors who treat arthritis and related disorders); neurologists and neurosurgeons (doctors who treat diseases of the nervous system); orthopedic surgeons (doctors who treat problems with the bones, joints, and ligaments); and physical therapists.

As people age the amount of adverse spinal conditions tend to increase. For example, increases in spinal stenosis, such as central canal and lateral stenosis, along with the thickening of the bones making up the spinal column and facet arthropathy are expected. Spinal stenosis typically includes a reduction in the available space for the passage of blood vessels and nerves which can impinge on these. Pain associated with such stenosis can be relieved by surgery. However, it is desirable to reduce the circumstances for which major surgeries are required to address stenosis.

The facet joints comprise part of the stability and mobility system of the human spine. The two facet joints compromise part of the posterior elements of the spine. They serve to limit translation of the spine but allow motion. There are nerves that service the capsule of the facet joints. The joints are a source of pain in many patients. Since they allow motion that can allow pain, fixation via stabilization can have benefits. Permanent fixation methods include metallic screws, wiring or bone grafting. Many techniques are destructive and can have adverse effects. Metallic implants can be rejected, broken, loosened, or improperly placed.

Facet fusion via the method and apparatus of the present invention can be accomplished with minimum additional risk or problems. Accordingly, it is desired to develop procedures and implants for surgically addressing stenosis through minimally invasive procedures, and preferably such surgical procedures can be performed on an outpatient basis. Spinal stenosis is an extremely common cause of problems across the world. Many patients undergo decompression surgery to treat the stricture of the spinal canal (i.e. stenosis). This surgery requires removal of bone and ligaments. This process can also be a common source of back pain. The term "glacial iatrogenic instability" applies to this scenario. Many patients undergoing a laminectomy procedure have pre-existing pain in their spine.

SUMMARY

The method and apparatus of the present invention is greatly useful for this subset of patients. The facet joints can easily be exposed during this type of surgery. The technique is incredibly simple when the joint is exposed.

In one embodiment a T-handled trocar is docked on the joint. A "stamp" which can be disposable can be placed in an inserter device. Once secure, this device is run down the trocar until it stops. In many circumstances the cortical bone, cartilage endplate and synovium will exit with the stamp. If it does not, a surgeon removes the stamp and places the graft holder on the inserter and replace down the trocar. The graft holder is closed to lock the debris in the graft holder for removal. The graft will then be placed in the graft holder and impacted when flush via a press fit in the track.

The novel design of the present invention is an improvement over other facet fusion devices. This device of the present invention will remove the cartilage, synovium and cortical bone. This allows the graft direct access to the cancellous bone on both sides of the facet joint to facilitate fusion. The design of the present invention provides a carpenter's shape that is more stable and will resist motion to thus aid in immediate back pain relief.

Many patients with spinal stenosis also have a condition called spondylolisthesis. This is slippage of one vertebral body on the one adjacent to it. Many of these patients will require decompression. The concern for this subset of patients after decompression is glacial instability. Facet fusion offers these patients stability without the necessity of spinal instrumentation. This thereby also allows for a reduction of additional surgery as this hardware often has to be removed at a later date.

Many patients complain of mechanical and facet driven back pain. The facet fusion procedure allows for mini-open versus percutaneous fusion procedure that is much less invasive than standard fusion surgery. This graft can be implanted via the standard instruments and fluoroscopic guidance. This gives patients an opportunity for pain relief without metallic implants and decreases operative time and blood loss.

Another subset of patients who benefit from the technique of the present invention are patients with recurrent disc herniation. The present invention allows for a less invasive and rapid stabilization method and should decrease the risk of additional disc herniation.

The graft and method of the present invention can also be used in concert with standard fusion techniques. By fixating the facet joints, this will augment standard instrumented and non-instrumented fusion.

The graft of the present invention can be machined cortical allograft. It serves to lock the two surfaces of the facet joint together in a way that decreases motion immediately and thereby decreases back pain. The bone will then go on to arthrodesis.

In one embodiment the instrument set of the present invention can be comprised of a T-handled trocar, an inserter, a disposable stamp or cutter, and a disposable graft holder. The graft will be sterile and can be packaged as a single unit. In one embodiment the device can be used in the thoracic and lumbar spine. In one embodiment bilateral grafts can provide optimum efficiency. In one embodiment only a single side can be grafted.

In one embodiment the method and apparatus benefits the patient, hospital, and surgeon. It offers a less invasive option for treatment of back pain. It is quick, simple and has immediate efficacy. Complication from implantation should be nominal. The cost savings to the hospitals is tremendous when compared to traditional methods.

One embodiment provides a minimally invasive method and apparatus for spinal facet joint fusion using irregularly shaped bone implants or bone screws which are positioned and then implanted in the direction of the facet plane.

One embodiment includes using an allograft such as donated human cadaver bone recovered from a donor's leg, and processed by a tissue bank. Preferably, it is recovered from the hard, or cortical, part of the largest leg bone, or femur. One embodiment includes using bone from animal bone. One embodiment includes using a material which is biodegradable in the body.

One embodiment includes minimally invasive spine surgery such as an arthroscopic type portal or open facet joint fusion surgical instrumentation for insertion of either premade, pre-shaped synthetic irregularly shaped bone implant or graft, or harvested and compacted iliac crest grafts, autologous or cadaveric allografts which are irregularly shaped.

In one embodiment the method and apparatus can be used on one or more of the forty-eight facet joints located on the spine (i.e., C1-C2 through L5-S1).

The use of an irregularly pre-shaped, harvested or synthetic bone as a structural fixation for facet joint fusion has the advantage of using bone instead of metal allowing for natural bone ingrowth and a stronger, permanent fusion; and (2) the natural or synthetic graft cannot work its way loose over time, a concern with screw type fixation.

One embodiment includes the use of a minimum invasive or an arthroscopic type portal for stand-alone procedures.

One embodiment includes use of an irregularly shaped bone implant as an adjunct to other fusion techniques.

One embodiment includes the use of a shaped bone implant having a plurality of arms and valleys (such as in the shape of an "X" or "cross" with rounded valleys and edges).

In one embodiment, the method and apparatus includes: (a) providing a positioning selector that allows the visual selection of the relative rotational angular and Cartesian coordinate position of the implant to be placed relative to the facet joint along the length of a facet joint or in the plane of the facet joint (i.e., taking materials from both the superior and inferior portions of the facet joint); (b) placing a guide tool which maintains such selected rotational angular position along with the selected Cartesian coordinate position; (c) using a cutting tool which makes an opening in the spine corresponding to the chosen relative position; and (d) inserting an irregularly shaped bone implant in the bone where the irregularly shaped bone implant also maintains the corresponding rotational angular position.

One embodiment includes the use of a positioning selector for allowing the visual selection of the relative rotational angular and Cartesian position of the implant to be implanted.

One embodiment includes the use of a guide tool for maintaining the selected relative rotational angular and Cartesian position during the process of cutting the opening for the implant and then implanting the implant.

One embodiment includes the use of a guide tool for guiding a cutter during the process of forming the graft opening or bore, and for stopping the cutter when the graft opening or bore reaches a predetermined depth.

In one embodiment the guide tool and cutter include a plurality of indicia which visually indicate the extent depth of the opening for the implant.

In one embodiment the cutter includes a tapered portion so that the average cross sectional area of the opening or bore decreases as the depth increases. In one embodiment the graft also has a tapered portion tracks or follows the tapered portion of the opening or bore.

One embodiment includes the use of an implant insertion tool which holds the implant and maintains a relative rotational angular position between the implant and the guide tool so that the selected relative rotational angular position selected for the implant is maintained and so that the implant can be inserted into the opening of bore made by the cutter.

One embodiment includes the use of an impacting tool or driver which can be used to separate the implant from the implant insertion tool. In one embodiment the relative angular position between the impacting tool and the implant is not constrained and can change.

One embodiment includes the use of an insertion guide and stop for limiting the depth of the driver during the process of inserting the bone graft into the opening or bore, and for stopping the bone implant when the depth of implant reaches a predetermined depth.

One embodiment includes one instrument for guiding and stopping for each of the above specified activities.

One embodiment provides a method and apparatus for relieving pain by relieving the pressure and restrictions on the blood vessels and nerves associated with the spine. This can be accomplished using a method and apparatus for spinal facet joint fusion using irregularly shaped bone implants or grafts which fuse two or more vertebrae in order to alleviate the problems caused by spinal stenosis, facet arthropathy, and similar conditions.

One embodiment provides a method and apparatus for spinal facet joint fusion using irregularly shaped bone implants or grafts comprising a plurality of facet joint implants or grafts positioned between the facet joints between the upper portion of the facet joint and the lower portion of the facet joint of a first vertebra and a second vertebra.

One embodiment provides a method and apparatus for spinal facet joint fusion using irregularly shaped bone implants or grafts for relieving pain due to conditions such as spinal stenosis and facet arthropathy. The method includes the steps of accessing adjacent first and second vertebrae of the spinal column and using irregularly shaped bone implants or grafts to fuse the facet joints between these vertebrae to relieve pain.

One embodiment includes a method and apparatus for spinal facet joint fusion using irregularly shaped bone implants or grafts to be able to accommodate the anatomical structure of multiple vertebrae and different sizes of facet joints for vertebrae.

One embodiment includes an irregularly shaped allograft cortical bone screw and matching die and tap system to achieve a secure fit for posterior fixation and permanent fusion.

One embodiment includes a minimally invasive surgical technique using conventionally available dilating or retraction systems or open surgery with a cutting guide and driving tool for cutting the opening for the implant or graft into the facet joint to achieve fusion. Minimally invasive (or minimally destructive) surgical techniques use small incisions and techniques to spread muscle and tissue rather than cutting through these when reaching the area to be surgically treated. These techniques result in less blood loss, risk, and postoperative pain, less physical therapy, and rehabilitation; allowing patients to recover more quickly.

One embodiment includes the implant being inserted in a non-traumatic fashion, and avoiding the risks of neural contusion, and rupture of the implant during the implantation process.

One embodiment includes an implant which has physical characteristics similar to the bone in which it is being implanted to facilitate grafting and minimal stresses on the fused vertebrae facets.

One embodiment uses harvested human bone, or cadaveric allograft.

One embodiment provides temporary fixation while the body's natural healing process permanently fuses the joint together by growing natural bone into the threaded member.

One embodiment includes a method and apparatus for facet fusion with reduced hospital (or outpatient time) and faster recovery time based on the methods minimally invasive properties.

One embodiment includes the cutting of an irregularly shaped opening in the plane of the facet joint of a specific level between superior and inferior facet surfaces. This bore is die cut such as by using a die tool. A matching irregularly shaped implant (matching shape to the cut and being of a cortical bone implant) is then placed (e.g., pushed) into the graft opening completing the fusion of the facet joint. Over time the implant will fuse together with the superior and inferior facet surfaces.

One embodiment includes the tapping or cutting of another opening in the plane of the second facet joint of the specified level between superior and inferior facet surfaces where a second irregularly shaped implant (cortical bone implant or screw) is then placed (e.g., pushed) into this second opening completing the fusion of this second facet joint. The irregular shape of the implants increase the contact area between the spine and the implant (thus decreasing the overall fusion time), and also resists differential rotation between the upper and lower portions of the facet joint. The irregular shape is also believed to reduce the risk that the implant will extrude out of the fusion site.

In one embodiment two irregularly shaped implants for each level of fusion are used.

In one embodiment one of both of the openings bores in the facet joints of a specified level are of differing irregular shapes. In one embodiment both are the same irregular shape.

In one embodiment stops and/or guides are provided on the implant tooling to ensure that the implant will not penetrate the foramen.

In one embodiment the implants for a specified level are stand alone fusion devices. These can be used to treat adjacent segment disease, degenerative joint disease of the facets or asteoarthritis.

In one embodiment the implants for a specified level are used to supplement posterior fusion techniques (such as cages).

In one embodiment the implants for a specified level are used to supplement anterior fusion techniques.

In one embodiment facet joint fusion can be used for decompression and laminectomy instead of another fusion system.

In one embodiment facet joint fusion can be used to supplement posterior fusion systems when a corpectomy has been performed.

In one embodiment facet joint fusion can be used in connection with instrumentation to correct scoliosis.

In one embodiment average surgical times for each level of fusion can be less than 60 minutes, less than 45 minutes, less than 30 minutes.

In one embodiment the method and apparatus can be used for C1-C2 through L5-S1.

In one embodiment the angle of approach of the cutting tool is posterior straight into the facet joint.

In one embodiment, at a specified level, the opening or bore of the first facet joint passes through the first facet joint and the bore of the second facet joint passes through the second facet joint.

In one embodiment, at a specified level, the angle of the opening or bore of the first facet joint is the same as the angle of the opening or bore of the second facet joint.

In one embodiment, at a specified level, the angle of the opening or bore of the first facet joint is different from the angle of the opening or bore of the second facet joint.

In one embodiment the opening or bore is made in the central portion of the facet joint. In one embodiment the opening or bore is shifted over such as ⅔ to one side and ⅓ to the other side.

In one embodiment the angle of approach does not fully comprise the joint and other instrumented options are available.

In one embodiment one or more CT scans can be used to determine bore depth to be stamped or prepared. In one embodiment bore depth can be less than or equal to 50 percent of the smallest facet surface area.

In one embodiment less than or equal to fifty percent of the facet joint is consumed in making the bore.

In one embodiment the method and apparatus can be used in place of a facet screw system.

In one embodiment the method and apparatus can be used to augment an anterior spinal fusion technique.

In one embodiment the method and apparatus can be used to augment a posterior spinal fusion technique.

In one embodiment the method and apparatus can be used as a stand alone posterior fusion.

One embodiment comprises the following steps:

(a) localize the facet joint either by direct visualization during open surgery or indirectly by fluoroscopy;

(b) remove the posterior capsule as well as any significant osteophytes or bone spurs (which can get back down to the original joint level without compromising the native bone);

(c) if necessary, clear the facet joint of any remaining cartilage of debris, such as with an arthroscopic rasp, or one millimeter burr and in line with the facet joint angle (i.e., in the same plane);

(d) place a positioning selector over the facet joint to select the position of the implant (relative rotation and Cartesian);

(e) place the guide tool over the positioning selector;

(f) remove the positioning selector;

(g) insert the cutting tool into the guide tool to cut an implant opening in the facet joint (such as in the plane of the facet joint);

(h) remove the cutting tool;

(i) insert plug removal tool (if needed);

(j) remove plug (or pieces of plug)

(k) insert an implant and implant holding tool into the guide tool until the implant at least partially enters the opening in the facet joint;

(l) insert an impaction tool into the guide tool to further insert the implant into the opening of the facet joint and detach the implant from the guide tool and implant holding tool; and (m) repeat the above steps for the second facet joint at the same level;

In one embodiment the irregularly shaped implants restrict the spinal facet joint surfaces at a specified level from moving relative to each other, and thereby allow the surfaces to graft together over time for permanent fusion.

Various embodiments of the method and apparatus can be used to fuse facet joints thereby alleviating impingements and/or restrictions on vessels and nerves associated therewith, and reducing pain caused by such restrictions.

In one embodiment creation and of a surgically cut bore or opening in a facet joint is accomplished without creating tiny bone fragments (such as that caused by drilling) which can migrate into other parts of a patient's body.

In one embodiment a stamp or cutter can be used to cut through sonovial and/or cartilage materials along with the bone in creating a surgically cut bore or opening in a facet joint for an insert, implant, or plug.

In one embodiment a stamp or cutter can be used to cut through sonovial and/or cartilage materials along with the bone in creating a surgically cut bore or opening in a facet joint for an insert, implant, or plug wherein no substantial amount of sonovial and/or cartilage material is mixed in and/or remains in the bore or opening thereby enabling pure bone to bone contact between the insert, implant, or plug and the surgically cut opening or bore thereby increasing the fusion between the portions of the vertebrae forming the facet joint and the insert, implant, or plug and speeding up the patient's recovery from the fusion.

In one embodiment a press fit is made between the surgically cut opening or bore and the insert, implant, or plug placed or fit into the opening or bore.

In one embodiment various advantages exist over conventional systems.

One embodiment includes a grafting system using a cutter to remove the synovium, cartilage and cortical bone at the interface of the facet joint. This allows the medullary bone to be exposed directly to the allograft.

In conventional systems drilling tend to push debris (cartilage and synovium) into the medullary channels (trabeculae). The basic tenet of maximum surface area of graft to host bone contact is achieved in this fashion. Currently available systems use drills to ream out a tract for graft insertion, thereby plugging many channels of viable boney surface area for fusion. This process can inhibit the fusion process.

Various embodiments uses unique shapes to avoid graft extrusion and provide better host bone to graft bone contact. Existing systems utilize round graft shapes. Due to the forces applied to the joint due to human motion in an upright model, many of these grafts can extrude.

In one embodiment is used an hourglass design which places the "ends of the hourglass" firmly in the opposite sides of the facet joint. The leading end of the graft has a taper to allow for slight over sizing of the graft to account for shrinkage issues with individual donors. It also allows for ease of graft insertion during the "press fit" process.

In one embodiment a ridge can be added to the non leading end of the bone graft to engage the joint and add another "buttress" feature to prevent graft extrusion.

In one embodiment the method and apparatus utilizes disposable bone cutters to avoid the risk of disease transmission. Conventional techniques use non-disposable drill bits that can, if improperly cleaned, lead to disease or infection transmission.

In one embodiment the method and apparatus requires no motorized power source, leading to decreased operative time if the power to the drill is compromised.

In embodiment it is recommended that the facet joint locator instrument be used to locate the angle or orientation of the facet joint to promote proper alignment, and avoid misalignment, of the implant, insert, or plug.

In one embodiment will be included a cannulated version to allow for true percutaneous implantation.

While certain novel features of this invention shown and described below are pointed out in the annexed claims, the invention is not intended to be limited to the details specified, since a person of ordinary skill in the relevant art will understand that various omissions, modifications, substitutions and/or changes in the forms and details of the device illustrated and in its operation may be made without departing in any way from the spirit of the present invention. No feature of the invention is critical or essential unless it is expressly stated as being "critical" or "essential."

BRIEF DESCRIPTION OF THE FIGURES

FIG. 1 is a side fragmentary view of a guide tool which can be used in the method and apparatus;

FIG. 2 is an end view taken along lines 2-2 of FIG. 1;

FIG. 3 is a sectional view taken along lines 3-3 of FIG. 1;

FIG. 4 is a sectional view taken along lines 4-4 of FIG. 1;

FIG. 5 is a top view taken along lines 5-5 of FIG. 1;

FIG. 6 is a side fragmentary view of the preferred embodiment of the apparatus of the present invention showing the cutting tool assembly;

FIG. 7 is a top view taken along lines 7-7 of FIG. 6;

FIG. 8 is an end view taken along lines 8-8 of FIG. 6;

FIG. 9 is an end view taken along lines 9-9 of FIG. 6;

FIG. 10 is a fragmentary view of the preferred embodiment of the apparatus of the present invention showing the cutter;

FIG. 11 is a sectional view taken along lines 11-11 of FIG. 10;

FIG. 12 is an end view taken along lines 12-12 of FIG. 10;

FIG. 13 is a partial perspective view of the preferred embodiment of the apparatus of the present invention showing the cutter;

FIG. 14 is a fragmentary side view of the preferred embodiment of the apparatus of the present invention showing the holder;

FIG. 15 is a perspective exploded view of the preferred embodiment of the apparatus of the present invention showing steps in assembling the cutting tool assembly;

FIG. 22 is a side view of the preferred embodiment of the apparatus of the present invention showing the tool for holding and inserting insert, implant, or graft;

FIG. 23 is a side view of the preferred embodiment of the apparatus of the present invention showing the impaction tool for dislodging the insert, implant, or graft from the tool of FIG. 22 and into the opening or bore of the facet joint made by a cutting tool;

FIG. 24 is an end view taken along lines 24-24 of FIG. 22;

FIG. 25 is a sectional view taken along lines 25-25 of FIG. 22;

FIG. 26 is a sectional view taken along lines 26-26 of FIG. 22;

FIG. 27 is an end view taken along lines 27-27 of FIG. 22 with stop collar omitted for clarity;

FIG. 28 is a fragmentary view of the preferred embodiment of the apparatus of the present invention and showing the insert, implant, or graft;

FIG. 29 is an end view taken along lines 29-29 of FIG. 28;

FIG. 30 is a side view illustrating the insert, implant, or graft;

FIG. 31 is a side view illustrating an alternate embodiment of the insert, implant, or graft;

FIG. 32 is a perspective view of the insert, implant, or graft shown in FIGS. 28-30;

FIG. 38 is a partial perspective view of the preferred embodiment of the apparatus of the present invention showing the grabbing tip of the plug or coupon removal tool;

FIG. 39 is an exploded perspective view of the preferred embodiment of the apparatus of the present invention indicating the steps of assembling the various components of the plug or coupon removal tool;

FIG. 40 is a sectional view of the plug or coupon removal tool of FIG. 38;

FIG. 41 is a perspective view of a template or gauge that is used with the plug or coupon removal tool of FIGS. 38-40;

FIG. 42 is a perspective view of an assembled plug or coupon removal tool of FIGS. 38-41;

FIG. 43 is a perspective view of the plug or coupon removal tool of FIGS. 38-41 illustrating the step of using the gauge or template of FIG. 41 to size the grabbing tip of FIG. 38 which grabbing tip can then be used to grab and remove the plug or coupon which had been cut using a cutting tool;

FIG. 44 is a perspective view of the remove tool of FIGS. 38-41 showing the gauge or template being removed from the now sized grabbing tip;

FIG. 47 is an elevation view of the preferred embodiment of the apparatus of the present invention illustrating plug or coupon removal where the grabbing tip of the plug or coupon removal tool is being placed of the cut section of the plug or coupon in the facet joint;

FIG. 48 is an elevation view of the preferred embodiment of the apparatus of the present invention illustrating plug or coupon removal where the grabbing tip of the plug or coupon removal tool has been placed of the cut section of the plug or coupon in the facet joint;

FIG. 49 is an elevation view of the preferred embodiment of the apparatus of the present invention illustrating plug or coupon removal where the grabbing tip of the plug or coupon removal tool is being squeezed over the cut section of the plug or coupon in the facet joint;

FIG. 50 is an elevation view of the preferred embodiment of the apparatus of the present invention illustrating plug or coupon removal where the squeezed grabbing tip of the plug or coupon removal tool pulling out the cut section of the plug or coupon leaving a bore or opening in the spine of the patient around the facet joint;

FIG. 51 is a sectional view of the bore or opening taken along lines 51-51 of FIG. 50;

FIG. 53 is a fragmentary side view of an alternate cutting tool which can also be used as the plug or coupon removal tool;

FIG. 54 is a side fragmentary view showing an optional handle for use with the alternate plug or coupon removal tool;

FIG. 55 is a side view showing an alternate cutter for use with the alternate plug or coupon removal tool;

FIG. 56 is a fragmentary perspective view showing the alternate cutter of FIG. 55;

FIG. 57 is a fragmentary side view showing part of the plug or coupon removal tool;

FIG. 58 is a fragmentary side view showing threaded wedging member portion of the alternate plug or coupon removal tool;

FIG. 69 is a side view of a facet joint locator having at least one longitudinal positioning line;

FIG. 70 is a sectional view of the facet joint locator of FIG. 69 taken along the lines 70-70 of FIG. 69;

FIG. 71 is a perspective view of the facet joint locator of FIG. 69.

FIG. 76 is a perspective view of an insert, implant, plug, or graft being placed in one embodiment of the insertion tip of the method and apparatus in which a portion of the insert extends outside of the insertion tip;

FIG. 77 is a sectional side view of the insertion tip placing the insert, implant, plug, or graft into the opening or bore previously made around the facet joint of a person's spine where the orientation of the insert, implant, plug, or graft is maintained with the opening or bore based on the orientation of the original facet joint locator shown in FIG. 75; and FIG. 78 is a sectional side view where an insertion rod is used to fully push the insert, implant, plug, or graft into the opening or bore about the facet joint.

DETAILED DESCRIPTION

"Allograft" is the transfer of tissue between two genetically dissimilar individuals of the same species but genetically distinct.

"Xenogeneic" denotes individuals or cell types from different species and different genotypes, such as tissues from different species that are antigenically dissimilar.

The term "Graft" includes both an Allograft and/or a Xenogeneic unless specified otherwise.

Figure 16:
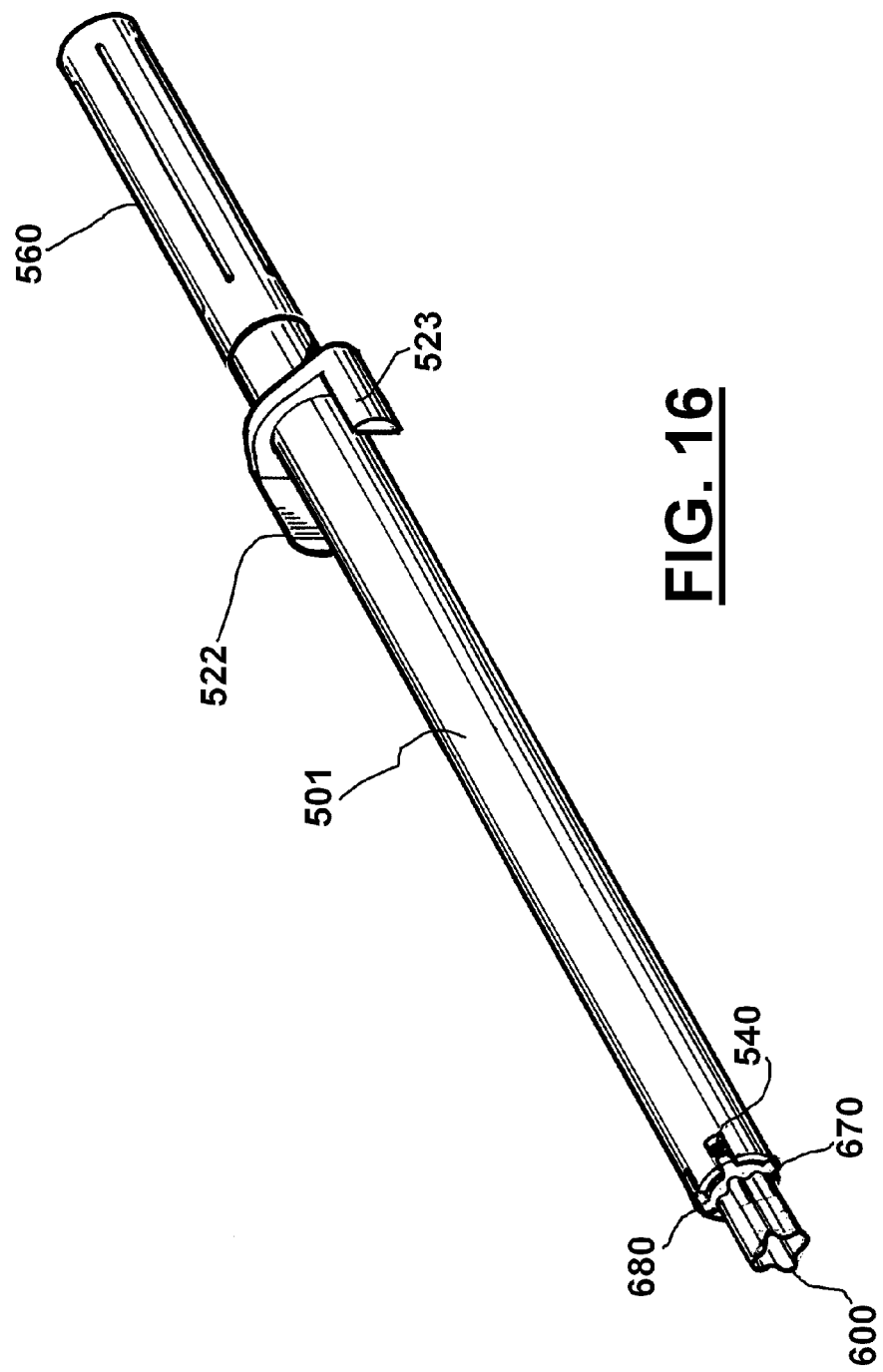
FIG. 16 is a partial perspective view of the preferred embodiment of the apparatus of the present invention showing the cutting tool assembly in an assembled condition.
Figure 17:
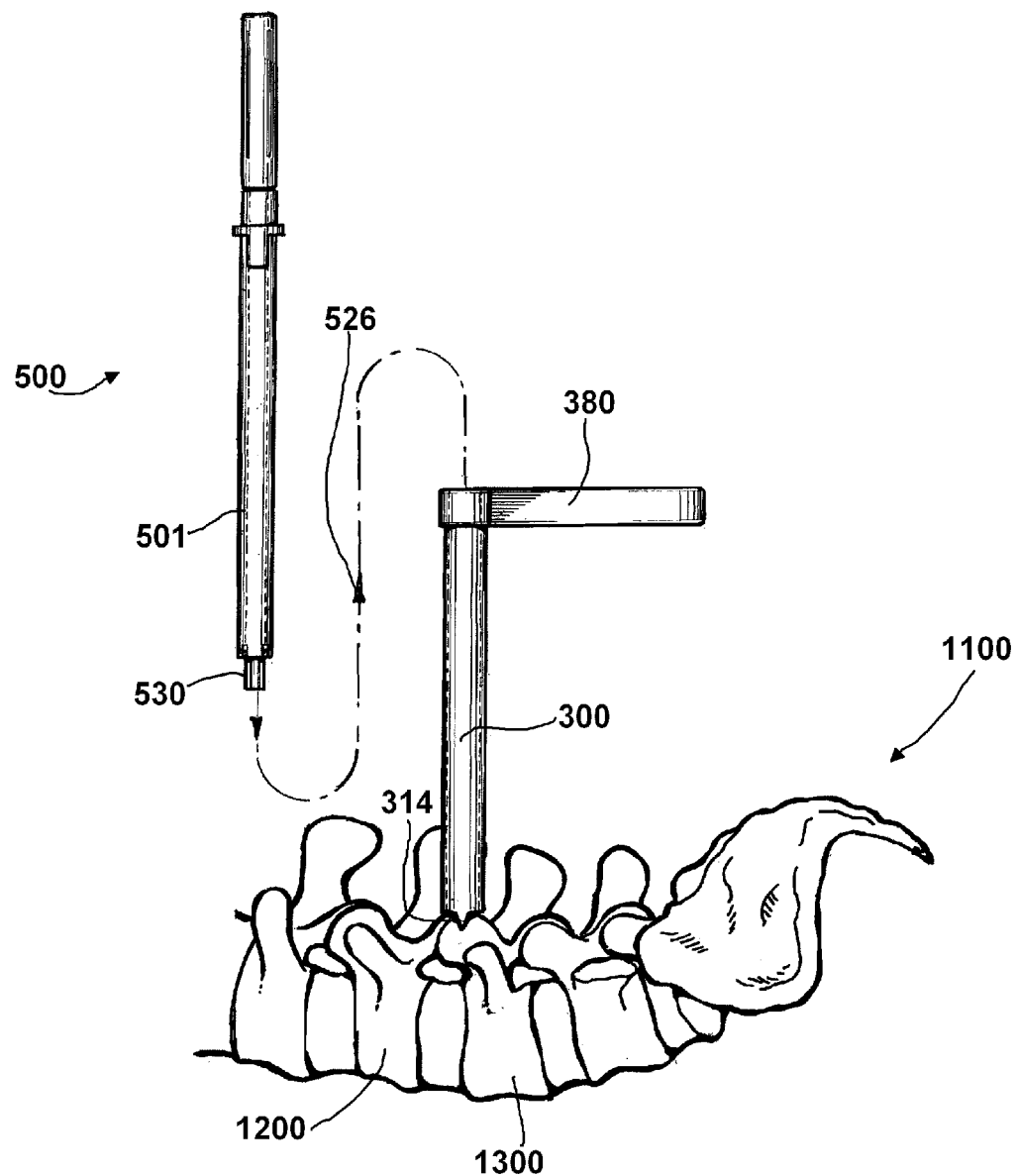
FIG. 17 is a schematic side elevation view of the preferred embodiment of the apparatus of the present invention illustrating placement of the guide tool of a facet joint, and insertion of the cutting tool assembly into the guide tool.
Figure 21:
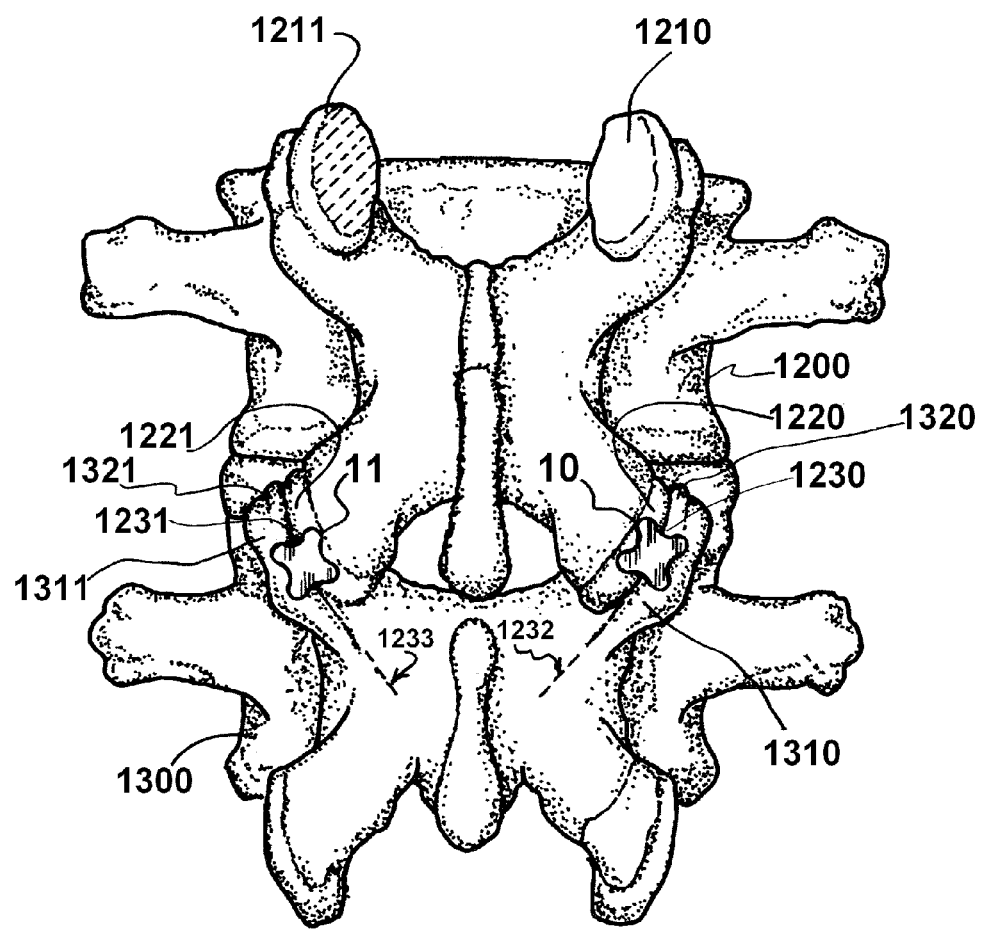
FIG. 21 is a perspective view of a patient's spine illustrating the facet joints and placement/location of two implants or grafts using the method of the present invention where the inserts, implants, or grafts span their respective facet joints.
Figures 36, 37:
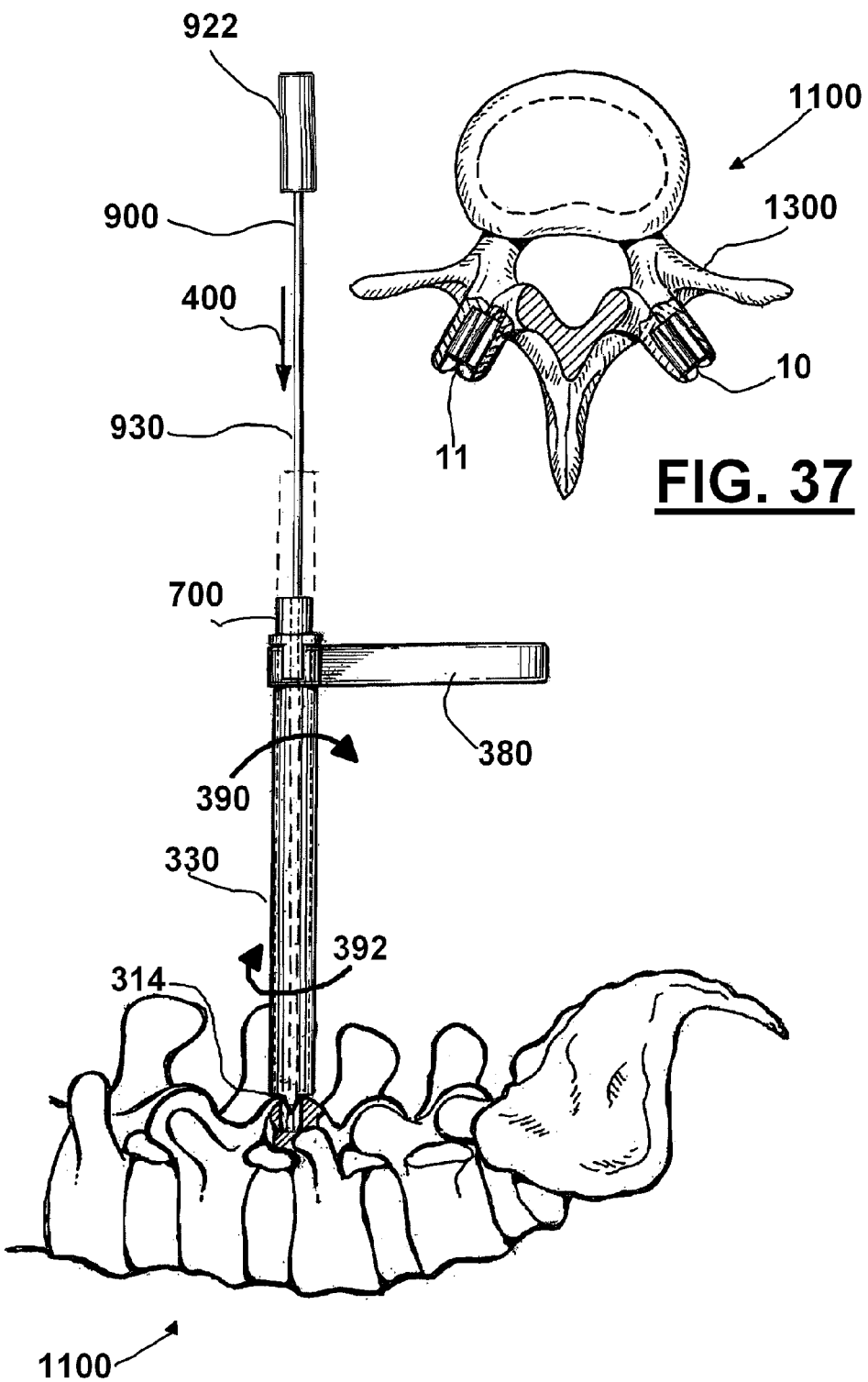
FIG. 36 is a schematic side view of the preferred embodiment of the apparatus of the present invention illustrating the insertion tool with insert, implant, or graft placed in an opening or bore of the facet joint and the step of using the impaction tool to push the insert, implant, or graft into the patient's spine at the facet joint.
FIG. 37 is a schematic view illustrating placement of two inserts, implants, or grafts in a patient's spine at the facet joints.

FIG. 17 is a perspective view of a portion of a spinal column 1100, along with a guide tool 300 having handle 380 just prior to insertion of cutting tool assembly 500 of upper and lower vertebrae 1200, 1300. In FIG. 21, two irregularly shaped implants 10, 11 are inserted in two sets of facet joints 1230, 1231. FIGS. 21 and 37 are sectional views of the lower vertebrae 1200, 1300.

Spinal column 1100 includes a plurality of vertebrae (including vertebrae 1200 and 1300). Spinal column 1100 also includes a spinal cord and nerve roots. In one embodiment the method and apparatus can be implanted to fuse together the facet joints of two or more sets of upper and lower vertebrae, which fusion can reduce pain caused by nerve root impingement or other problems with the spinal column by fusing the two vertebrae and restricting relative movement between the two vertebrae.

As will be discussed below, irregularly shaped inserts or implants 10, 11 can be grafts which can be used to fuse together facet joints 1230, 1231. Facet joint 1230 can comprise lower portion 1220 of facet joint 1230 for vertebra 1200 along with upper portion 1310 of facet joint 1230 for vertebra 1300. Facet joint 1231 can comprise lower portion 1221 of facet joint 1231 for vertebra 1200 along with upper portion 1311 of facet joint 1231 for vertebra 1300.

After implantation of irregularly shaped inserts or implants 10 and 11 relative movement between vertebrae 1200 and 1300 will be restricted. Additionally, extended direct contact between vertebrae 1200 and 1300 will be achieved and maintained. Such direct contact will allow vertebrae 1200 and 1300 to fuse together at the points of direct contact by replacement and/or exchange of bone material.

Where implants are comprised of graft material then such fusion can also occur onto and through the implants. It is believed that the greater amount of contact surface area between live bone and a graft implant will increase and/or speed up the fusion process. Therefore, it is believed that an irregularly shaped implant with a large amount of surface area is preferred compared to a regularly shaped implant. Examples of regularly shaped implants can be cylinders and/or rectangles.

It is further believed that minimizing the amount of possible relative movement between the upper and lower vertebrae will accelerate the overall fusion process. It is believed that allowing relative movement with respect to the points of contact between the upper and lower vertebrae which are intended to be fused together will interrupt the fusion process at the areas where relative movement is allowed between the points of contact. In such places were relative movement is allowed and the fusion process is interrupted, the fusion process can be required to begin again as the earlier portion of any bone which was fused together has now been separated and must be reattached. Additionally, where relative movement occurs multiple times during the fusion process (breaking apart previously fused areas), the ultimate final fusion event may be weaker than compared to a fusion process where relative movement was restricted and/or prevented.

In one embodiment the irregularly shaped implants are shaped to restrict and/or prevent relative movement between upper and lower vertebrae. In one embodiment the implants can have a plurality of arms which are radially spaced about a longitudinal axis.

It is also preferred to avoid sharp edges in both the implant and the volume in which the implant is to be inserted to start the fusion process. Avoiding sharp edges is preferred because such sharp edges can act as stress concentrators which concentrations of stress can increase the risk that a mechanical fracture and/or failure occurs in the patient's vertebrae being fused and/or the implants being used to fuse the patient's vertebra. Accordingly, in one embodiment the implant has rounded edges in its outer periphery and inner valleys.

In one embodiment the implant is implanted so that it appears substantially symmetrical when intersected by the plane of the facet joint. In one embodiment the implant has a plurality of arms and an equal number of arms fall on one side of the plane of the facet joint as that falling on the opposite side of the plane of the facet joint.

In one embodiment, after implantation and before fusion, the relative rotation between the implant and the vertebrae being fused is mechanically resisted by forces other than friction. In one embodiment the implant and the vertebrae being fused have a dovetail relationship. Dovetailing can be a fan-shaped tenon that forms a tight interlocking joint when fitted into a corresponding mortise. Dovetailing can also be a joint formed by interlocking one or more such tenons and mortises.

In one embodiment an irregularly shaped implant 10 is provided. The selected size of the implant will be known by those of ordinary skill in the art based on the size of the vertebra to be fused together including the size of the facet joint for such fusion. Such size can be estimated by x-raying the joints to be fused and/or estimating based on the overall size of the patient.

Figure 33:
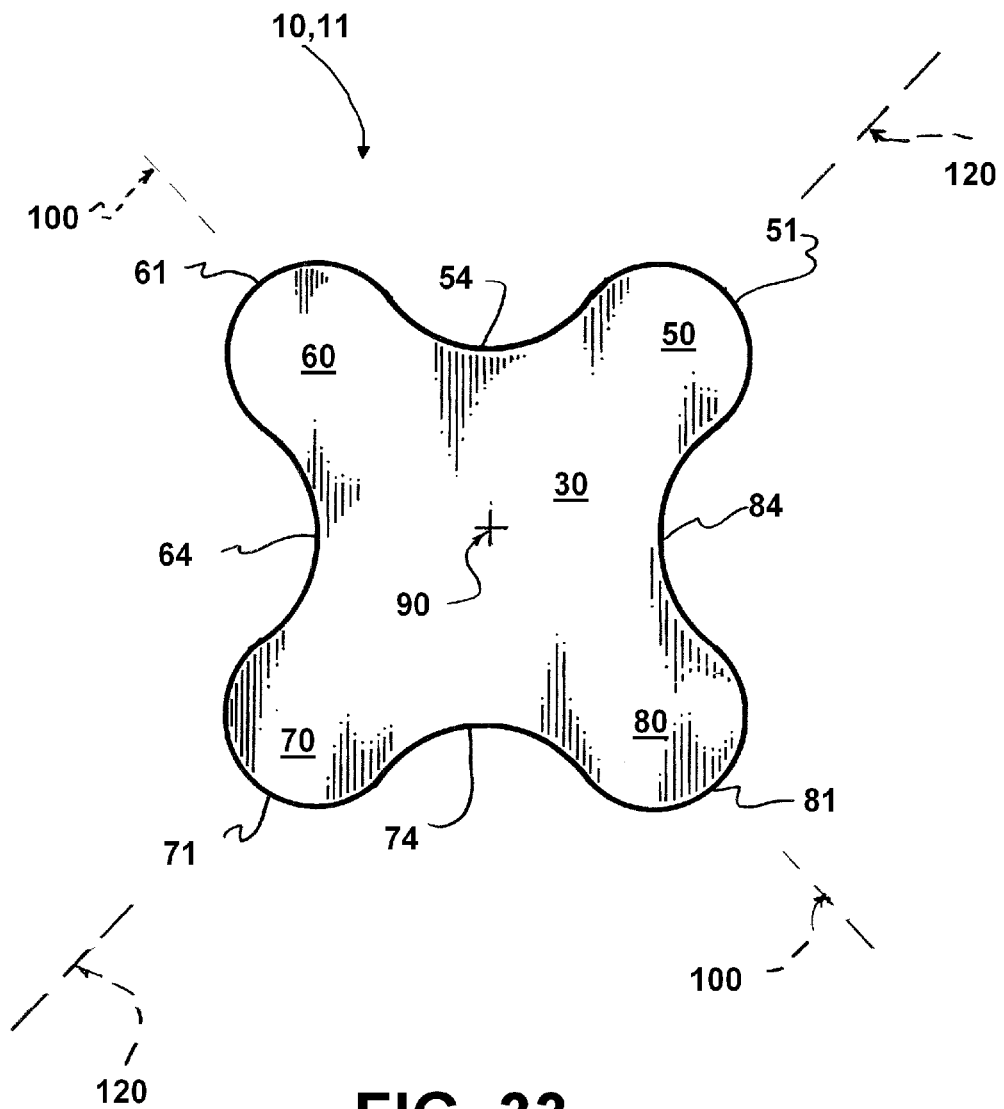
FIG. 33 is an end view of the insert, implant, or graft of FIGS. 28-30 and 32.
Figure 34:
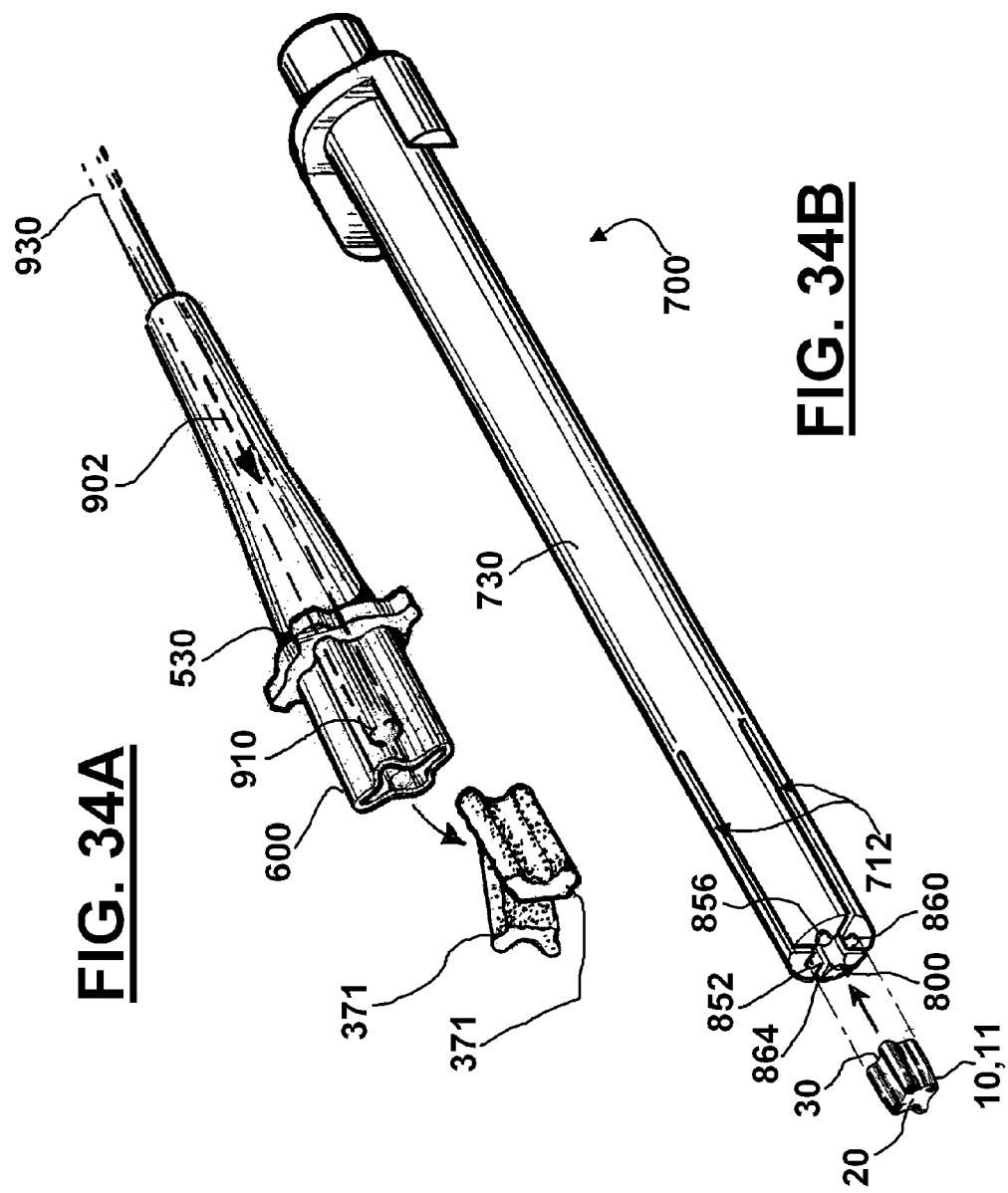
FIG. 34A is a perspective view illustrating removal of the cut or stamped out coupon or plug from a cutting tip of a cutting tool where the impaction tool of FIG. 23 can be used for pushing out the coupon or plug from the cutting tip.
FIG. 34B is a perspective view illustrating insertion of an insert, implant, or graft into the tool for holding the insert, implant, or graft.
Figure 35:
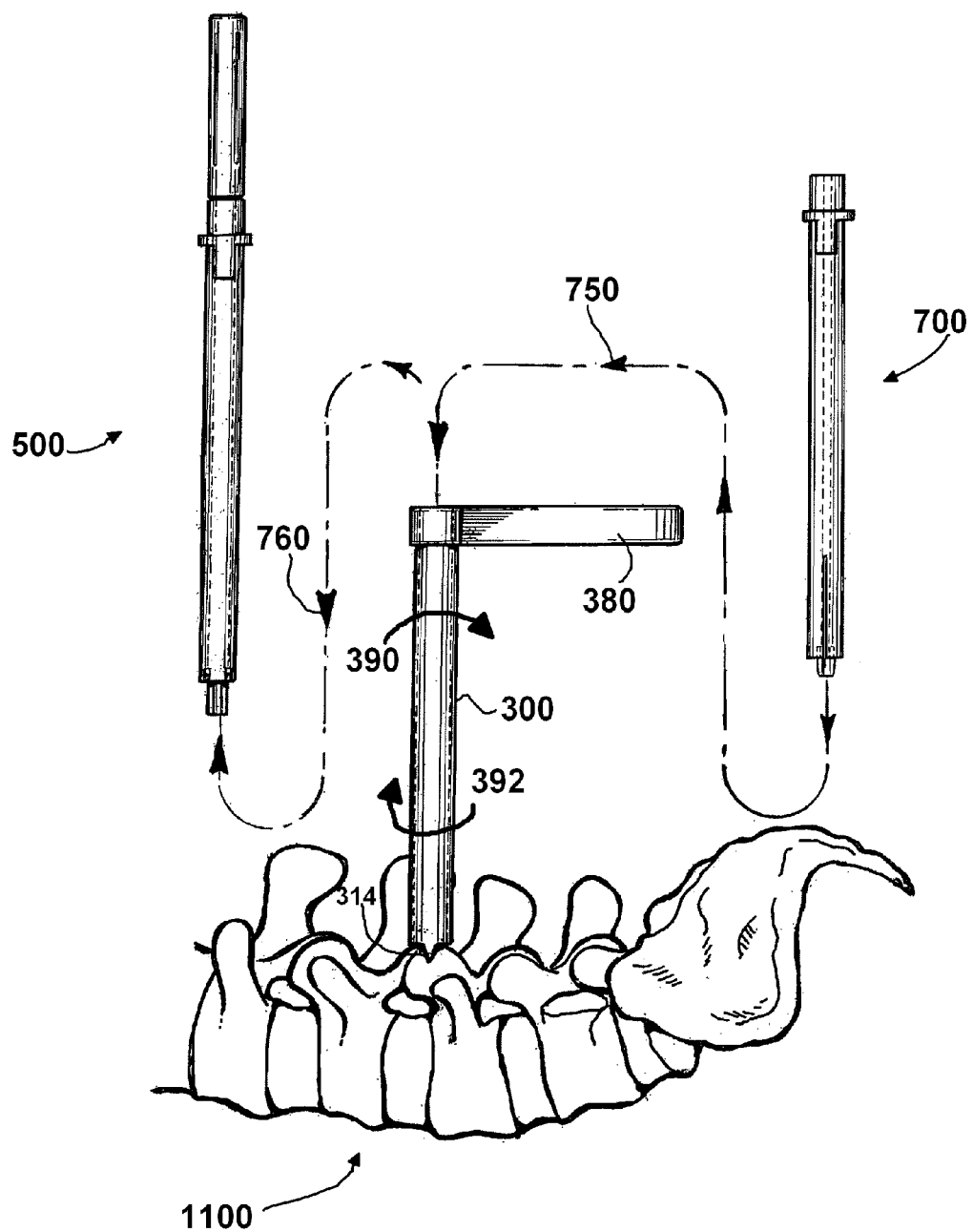
FIG. 35 is a schematic elevation view of the preferred embodiment of the apparatus of the present invention illustrating the steps of removing the cutting tool with cut out coupon (shown in FIG. 34A) and subsequently inserting the insertion tool holding insert, implant, or graft to be inserted (shown in FIG. 34B) where both the cutting tool and insertion tool and slide into and out of the guide tool.

In one embodiment implants 10, 11 can include a plurality of arms which are symmetrically disposed around the longitudinal axis of implants 10, 11, and a plane intersecting such longitudinal axis at a right angle creating a shape which is symmetric about at least one line which bisects at least one of the arms. Irregularly shaped is intended to exclude implants of a regular shape such as a cylinder and/or a rectangle or square. FIG. 32 is a perspective view of irregularly shaped implant 10 or 11. FIG. 29 is a front view of implant 10 or 11. FIG. 33 is an end view of implant 10 or 11.

Implant 10 can comprise first side 20 and second side 30. Each of the sides 20, 30 can be planar surfaces. Implant 10 can include a plurality of arms 50, 60, 70, 80 which are substantially radially disposed around longitudinal axis 92 which axis passes through center 90 and is substantially perpendicular to side 20 and side 30. Arms 50, 60, 70, 80 can respectively include tips 51, 61, 71, 81. Between arms 50, 60, 70, 80 can be valleys 54, 64, 74, 84. Tips 51, 61, 71, 81 and valleys 54, 64, 74, 84 are preferably rounded and include no sharp areas (to minimize stress enhancement). In one embodiment tapers 52, 62, 72, 82 can be provided so that the size of face 20 is actually smaller than the size of face 30. Tapering can facilitate insertion of implant 10 into an opening made in a facet joint.

Implant 10 can be constructed such that line 100 is a line of symmetry. Implant 10 can be constructed such that line 120 is a line of symmetry. Arms 50, 60, 70, 80 can be substantially the same size and shape. Alternatively Arms 50, 70 can be substantially the same size and shape; and arms 60, 80 can be substantially the same size and shape, but with the two sets of arms being of substantially different size and/or shape. For example the length of arm 50 can be longer than the length of arm 60; or the width of arm 50 can be smaller than the width of arm 60.

In one embodiment three arms are used. In one embodiment 5, 6, 7, 8, 9, 10, 11, or more arms are used. In one embodiment an odd number of arms are used. In one embodiment an even number of arms are used. Although not shown, in one embodiment one or more of the arms can increase in width from the valley to its tip. In FIG. 31, implant 21 can be of the same size and shape of implant 10, 11 but have spaced apart ridges 22 that help grip the surgically cut implant opening.

FIGS. 1-5 show guide tool 300. Guide tool 300 can be the tool used by the surgeon for maintaining the selected position of implantation (location, rotational position, and angular position) for implant 10. Guide tool 300 can comprise first end 310, body 330 and second end 320. On second end 320 can be attached handle 380 which handle can be used to selectively position guide tool 300. Body 330 can include thru opening 340 which extends from first end 310 to second end 320. Thru opening 340 can include rounded wall 360.

On first end 310 of guide tool 300, can be a plurality of insertion prongs 312, 314. Two insertion prongs 312, 314 are shown, but more can be used if desired. Insertion prongs 312, 314 are intended to dig into spinal column 1100 and fix the location of the ultimate point of insertion of implants 10, 11. The location is fixed by prongs 312, 314 connecting to the bone of spinal column 1100 (upper and lower vertebrae 1200, 1300). The selected Cartesian and rotational location is fixed by insertion prongs 312, 314. The angular location can be fixed by the surgeon holding handle 380 such that the angular position between guide tool 300 and the patient is maintained. However, the surgeon has a certain amount of flexibility in modifying the angular position of guide tool 300 (and ultimate angular position of implant 10) by moving guide tool 300 relative to the patient.

FIG. 21 is an anatomical drawing illustrating two vertebrae 1200, 1300. Shown are upper portion 1210, 1211 of a facet joint for vertebrae 1200. The lower portions 1220, 1221 of the facet joints 1230, 1231 for vertebrae 1200 are shown. Upper portions 1310, 1311 for facet joints 1230, 1231 are shown as are the upper portions 1310, 1311 of the facet joints 1230, 1231 of vertebrae 1300.

Insertion prongs 312, 314 assist in holding together upper and lower vertebrae 1200, 1300 during the remaining steps of creation of the opening for implant 10 insertion, and ultimately inserting implant 10. Preferably, at least one insertion prong (e.g., 312) will bite into upper vertebra 1200 and at least one insertion prong (e.g., 314) will bite into lower vertebra 1300. By this means upper and lower vertebrae 1200, 1300 will be fixed relative to each other (e.g., remain at a constant distance relative to each and not slide relative to each other) during the process of creating the opening for implant 10 for ultimate fusion between upper and lower vertebrae 1200, 1300. As will be described below (see FIG. 2), Line B-B which is in the middle of prongs 312, 314 is preferably aligned with plane 1232 of facet joint 1230 (or plane 1233 of facet joint 1231). In this manner upper portions 1310, 1311 of facet joints 1230, 1231 for vertebra 1300 can be held close to lower portions 1220, 1221 of facet joints 1230, 1231 for vertebra 1200 during the entire cutting and implantation process.

FIGS. 6-19 show bone cutting tool assembly 500. Bone cutting tool assembly 500 can be used to create an opening of proper size and location for insertion of implants 10, 11. Bone cutting tool assembly 500 can comprise body 505 with first end 510 and second end 520. On first end 510 can be positioned cutter 530 (which can be a replaceable cutting tip and/or allow cutting tips of different sizes and/or configurations). On second end 520 can be collar 512. Flange 670 in FIGS. 10-13 determine the depth of penetration of cutting tip 600. In one embodiment the length of body 530 can be a length substantially equal to the length of body 330 of guide tool 300, less the distance 640. Collar 512 has arms or flanges 522, 523. The arms or flanges 522, 523 are sized and shaped (e.g. curved) to closely conform to handle 380 of guide tool 300 (see FIGS. 17, 19). Thus, the radial position of guide tool 300 and its handle 380 determine the radial position of cutting tool assembly 500 once flanges 522, 523 interlock with handle 380 (see FIG. 17).

Figure 18:
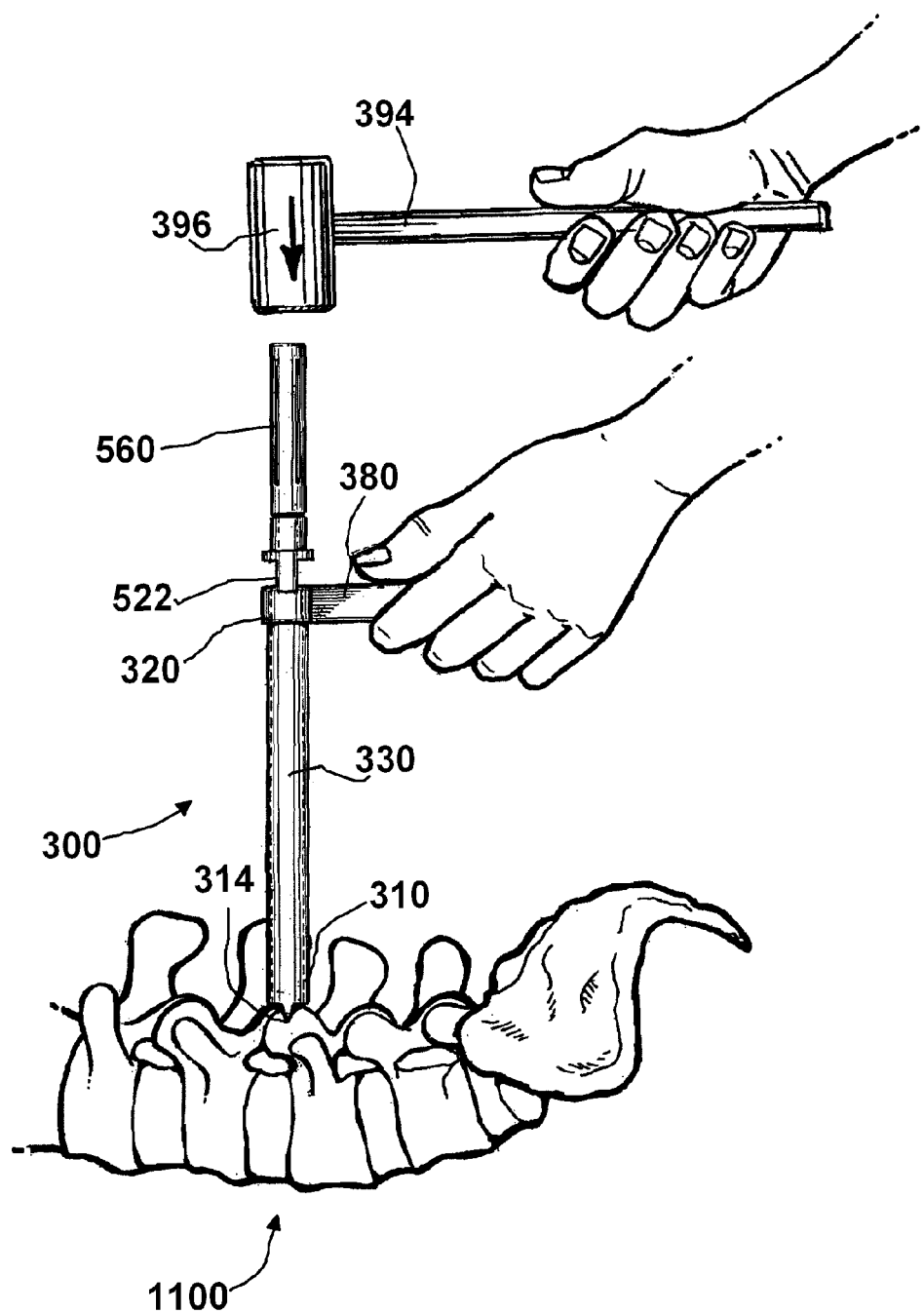
FIG. 18 is a schematic side elevation view of the preferred embodiment of the apparatus of the present invention illustrating placement of the guide tool and cutting tool assembly and force being applied to the cutting tool assembly to make an opening or bore in the facet joint.

Cutting tool assembly body 505 includes rounded portion 560 of sleeve 501 surrounding bore 524 (FIG. 8). On first end 510 can be circumferentially spaced apart slots 540. Cutter 530 (FIGS. 10-13) can be fitted to body 505 at slots 540. Cutter 530 can be a replaceable cutting tip and/or can be sized and shaped to allow cutting tips of different sizes. Cutter 530 can include cutting tip 600 having first end 610, second end 620 and prongs or arms 652, 656, 660, 664. Between these prongs or arms can be valleys 653, 657, 661, 665 which respectively are located between the arms. These prongs or arms can be sized to coordinate with implants 10, 11 so that the opening created by these prongs or arms will fit implants 10, 11. The relative rotational position between cutter 530 and cutting tool 500 can be maintained by ensuring that the projections 680 of flange 670 interlock with slots 540. In FIG. 18, mallet 394 applied flows (arrow 396) to handle 560 when cutting. Cutting tip 600 can have a depth 640 which can determine the depth of cut for the opening for implant 10 or 11.

Cutter 530 is shown as having an internally threaded area 622 so that it can be threadably connected to holder 550. Being externally threaded with threads 570 also allows holder 550 to be detachably connected to a coupon removal tool. Holder 550 has handle 560 and shaft 580. Cutter 530 can include first end 610 and second end 620. Cutting tip 600 can be tapered, which tapering can be sized to match any tapering of implant 10, 11. Alternatively, cutting tip 600 need not be tapered even where implant 10, 11 is not tapered.

In one embodiment, a plurality of cutting tips 600, 600', 600'', 600''', etc. of cutters 530 can be included which can be detachably connectable to cutting tool body 505 and holder 550 at shaft 580. Such plurality of cutting tips can be of different sizes and configuration if desired to match implants 10, 10', 10'', 10''', 10'''', etc. of different sizes and configurations. Additionally, a plurality of cutting tips which are detachably connectable to cutting tool 500 (even if of the same size and configuration) so that such cutting tips can be replaced after being used for a patient with an implantation surgery. Replacing only the cutting tips is believed to reduce the overall cost as no additional cutting tool 500 need be purchased. However, the various tools used in the implantation surgery should be cleaned and disinfected before and after any implantation surgery.

FIGS. 22-37 show implant holder and insertion tool 700. Tool 700 has first end 710, second end 720, and body 730. Body 730 can include opening or bore 740. Accordingly, once the position (location/Cartesian, rotational, and angular) of implantation is selected using prongs 312, 314 of guide tool body 330 this position will be maintained with respect to implant insertion tool 700. Body 730 can have a length which may be equal to or longer than the length of body 330 of guide tool 300.

On first end 710 can be an opening 800 with a depth 810 for receiving implant 10 or 11. Opening 800 can include prongs or arms 852, 856, 860, 864. Between these prongs or arms can be valleys (not labeled for clarity). These prongs or arms can be sized to coordinate with the shape or periphery of implant 10 or 11 (see FIGS. 29, 33) so that the opening having these prongs or arms will accept implant 10. It is preferred that the depth 810 of opening 800 be less than the depth or height 40 of implant 10 or 11 so that implant 10 or 11 will at least partially extend from first end 710. At least partially extending from first end 710 facilitates insertion of implant 10 into the opening made by cutting tool 500 in spinal column 1100.

Insertion tool 700 can include a plurality of slots or cutouts 712, each having a depth 714. These cutouts 712 facilitate the insertion and/or removal of implant 10 from opening 800 on first end 710. These cutouts 712 create a plurality of arms which act as cantilever springs so that the arms can relatively easily expand and accept implant 10 into opening 800. Additionally, these arms allow implant 10 to be relatively easily removed from insertion tool 700.

Insertion tool 700 can include an open ended bore or thru opening 740 extending from first end 710 to second end 720. Thru opening 740 can be cylindrical in shape. Thru area 740 can be sized to accept shaft or body 930 of impacting tool 900. Impacting tool 900 can include first end 910, second end 920, and body 930. Body 930 can have a length which may be equal to or longer than the length of body 330 of guide tool 300. On second end 920 can be attached handle 922.

For the method of the present invention, the goal is to implant an irregularly shaped implant 10 or 11 into a facet joint 1230 or 1231 between upper and lower vertebra 1200, 1300 of spinal column 1100 in a position and orientation (Cartesian location, rotational, and angular) selected by the surgeon. Generally, the method and apparatus includes an irregularly shaped implant 10 which is of a graft material and the mechanism to insert this implant into a patient's facet joint which will facilitate fusion between the upper and lower vertebrae of the facet joint while the implant resists relative movement between the upper and lower vertebrae of the facet joint.

Generally, the steps include (a) selecting an irregularly shaped implant; (b) selecting a position of implantation; (c) selecting an orientation for implantation; (d) creating an opening for implantation having such position and/or orientation; and (d) inserting the implant into the opening having such position and/or orientation. In one embodiment, the orientation includes a rotational orientation. In one embodiment the orientation includes an angular orientation. In one embodiment the implant includes a plurality of prongs or arms.

FIGS. 21 and 37 are diagrams schematically showing two irregularly shaped implants 10, 11 implanted in the facet joints 1230, 1231 of vertebrae 1200, 1300. The prongs or arms of these implants 10, 11 are shown only in schematic form. FIG. 37 is a cross section with the arms or prongs of implants 10, 11 shown only in schematic form. Such implants 10, 11 can either individually and/or in combination resist relative movement of vertebrae 1200, 1300 in various directions. Relative rotational movement between vertebrae 1200, 1300 can be resisted by the arms or prongs of the implants 10, 11. Additionally, relative angular movement (such as rotation along a line included in facet plane 1232 of facet joint 1230 where such line is perpendicular to the longitudinal axis of implant 10) can be resisted by the prongs or arms of implant 10 where these prongs or arms interlock with the opening created in the facet joint 1230 for implantation. Similarly, angular rotation can be resisted by implant 11 and facet joint 1231. Such resistance to relative movement is believed to shorten the overall fusion process between vertebrae 1200, 1300 by minimizing situations where relative movement could occur which could cause the fusion (e.g., grafting) process to be interrupted and/or slowed.

On first end 310 of guide tool 300, can be a plurality of insertion prongs 312, 314 which are intended to dig into spinal column 1100 preferably above and below a facet joint 1230 or 1231. This fixes the location of the ultimate point of insertion of implant 10 or 11 in facet joint 1230 or 1231. The location fixed by prongs 312,314 detachably attaches to the bone of spinal column 1100 (in both the upper and lower vertebrae 1200, 1300). The selected Cartesian and rotational location remain fixed by insertion prongs 312,314 into the bone of upper and lower vertebrae 1200, 1300.

The angular location can be fixed by the surgeon holding handle 380 such that the angular position between guide tool 300 and the patient is maintained. However, the surgeon has a certain amount of flexibility in changing the angular position of guide tool 300 (and ultimate angular position of implant 10 or 11) by moving guide tool 300 relative to the patient.

Insertion prongs 312,314 also assist in holding together upper and lower vertebrae 1200, 1300 during the remaining steps of creating the opening for implant 10, 11 insertion, and ultimately inserting implant 10 or 11. Preferably, at least one insertion prong (e.g., 312) will bite into upper vertebra 1200 and at least one insertion prong (e.g., 314) will bite into lower vertebra 1300. By this means upper and lower vertebrae 1200, 1300 will be fixed relative to each other (e.g., remain at a constant distance relative to each and not slide relative to each other) during the process of creating the opening for implant 10 for ultimate fusion between upper and lower vertebrae 1200, 1300. As will be described below Line B-B which is in the middle of prongs 312, 314 is preferably aligned with plane 1232 of facet joint 1230. In this manner upper portion 1310 of facet joint 1230 for vertebra 1300 can be held close to lower portion 1220 of facet joint 1230 for vertebra 1200 during the entire implantation process.

Figure 19:
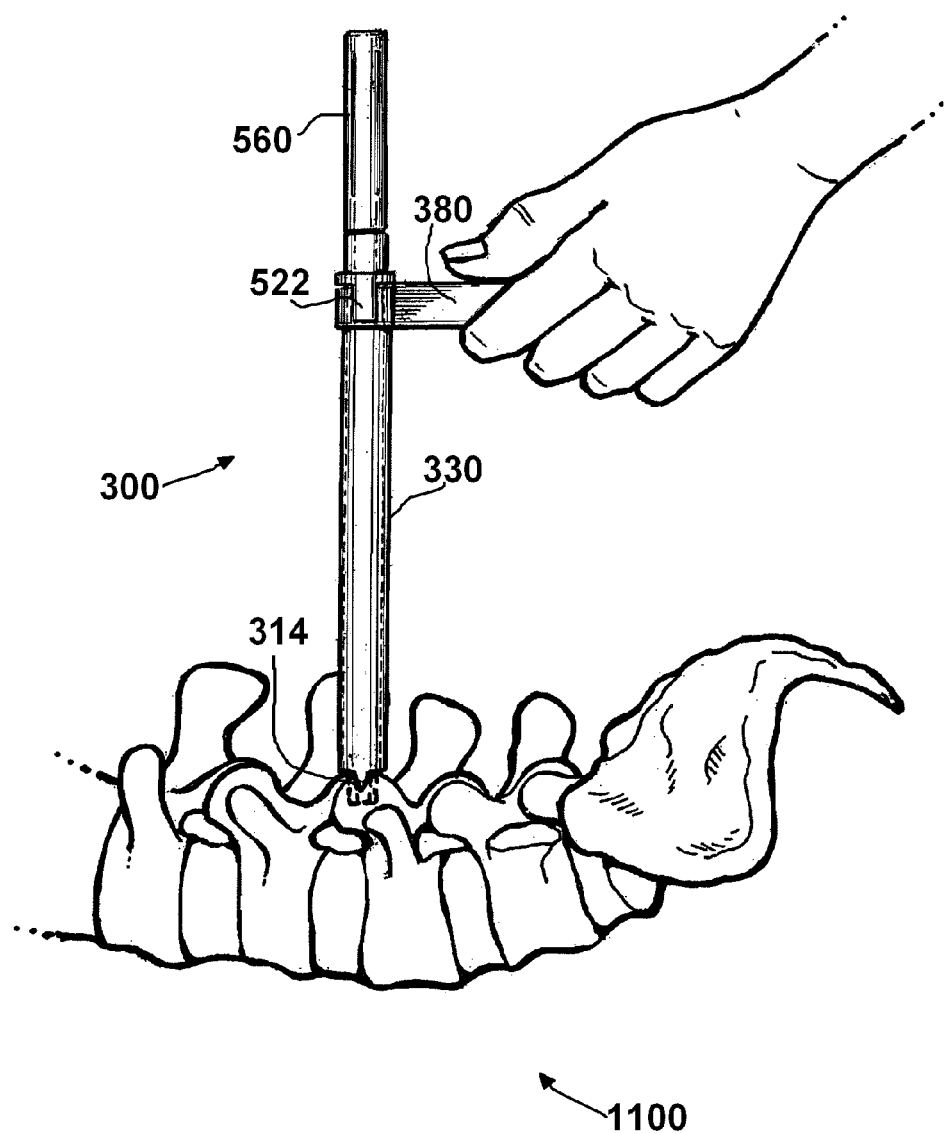
FIG. 19 is a schematic side elevation view of the preferred embodiment of the apparatus of the present invention at the end of the step illustrated in FIG. 18, and now illustrating completion of downward movement of the cutting tool assembly into the guide tool for making an opening or bore in the facet joint.
Figure 20:
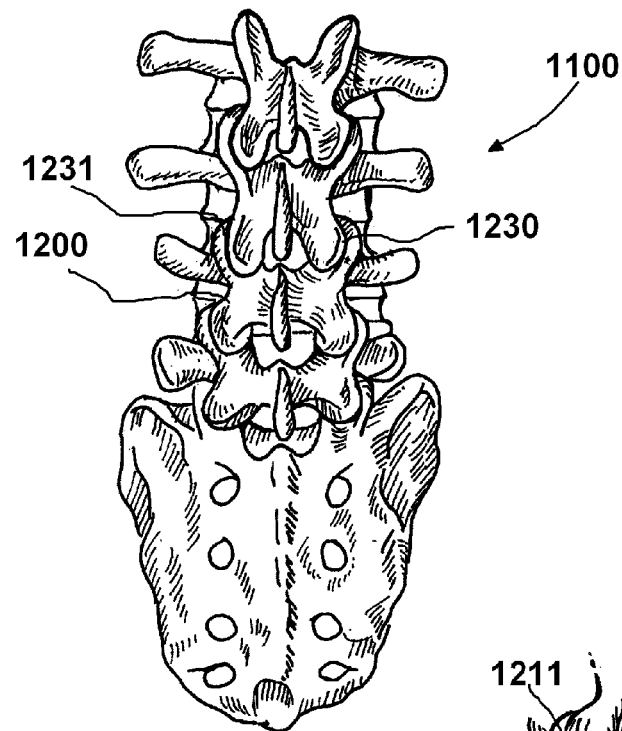
FIGS. 20-20A are perspective views of a patient's spine illustrating the facet joints and placement/location of an implant or graft using the method of the present invention where the insert, implant, or graft spans the facet joint on the left hand portion of the facet joint and the right hand portion of the facet joint does not have an implant or graft.
Figure 20A:
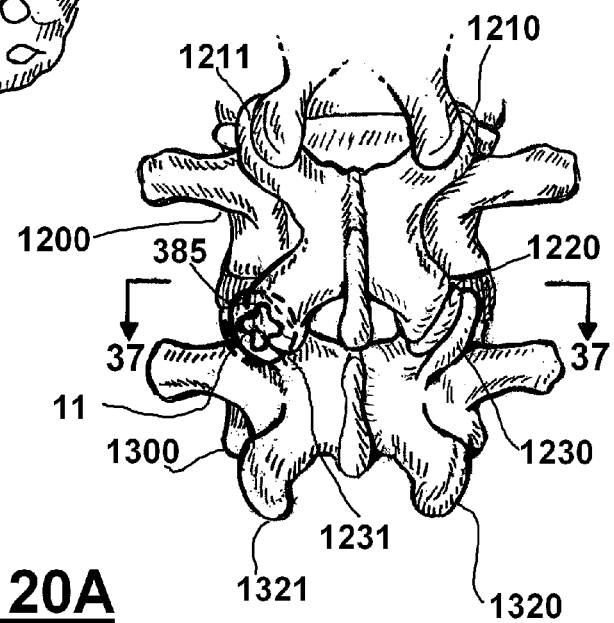

The next step will be creating the properly sized opening for implant 10 which can be made using cutting tool 500 with cutting tip 600. FIG. 18 is a side view of a cutting tool 530 with cutting tip 600 being inserted into the guide tool 300. To cause the opening for implant 10, 11 to be made cutting tip 600 is forced into the bone of spinal column 1100 through an application of force on handle 560. FIG. 19 is a side view of the cutting tip 600 completely inserted into the guide tool 300 and now having cut into the facet joint (not shown for clarity) via the cutting tip 600. Flanges 522, 523 are in contact with handle 380 of guide tool 300. Cutting tip 600 is extending out of first end 310 of guide tool 300 a distance 640. Distance 640 is the depth of opening made for implant 10. At this same time prongs 312, 314 remain fixed in the bone of spinal column 1100 to allow cutting tip 600 to make the proper sized opening.

After the opening for implant 10 has been made, cutting tool 500 can be removed by pulling on handle 560 and sliding cutting tool 500 out of guide tool 300. In some cases plug or coupon 371 will come out of the spine of patient along with cutting tool 500 such as by friction between cutting tool 500 and plug or coupon 371. However, plug or coupon 371 will not always come out with cutting tool and an additional step of plug or coupon removal will be required. Various embodiments can be used to remove the cut plug or coupon 371 as will be described below. For example, the grabbing plug or coupon removal tool assembly of FIGS. 38-40 could be used (which procedure is described below). As another example the threaded and wedging plug or coupon removal tool assembly of FIGS. 53-58 could be used (which procedure is also described below).

The next step in the process is inserting implant 10 or 11 into the surgically cut opening. Insertion of implant 10 or 11 can be greatly facilitated where the position of implant 10 or 11 (to be implanted) is coordinated (Cartesian location, rotational, and angular) with the position of opening for implant 10. Accordingly, in the next step an implant insertion tool 700 is used which can so coordinate the insertion of implant 10 into previously made opening.

FIGS. 22-37 show views of implant insertion tool 700 along with irregularly shaped implant 10 or 11. To cause implant 10 or 11 to be inserted into the opening for implant 10 or 11, insertion tool 700 is slid through opening 340 of guide tool 300. At this same time prongs 312,314 remain fixed in the bone of spinal column 1100 to allow insertion of implant 10 at the proper orientation relative to the opening for implant. Arrows 392 and 390 schematically indicate that rotational and angular remain fixed. FIG. 36 is a side view of the implant insertion tool 700 with irregularly shaped implant 10 completely inserted into the guide tool 300 so that the implant 10 is at least partially inserted into the opening previously cut into the facet joint (the facet joint not being shown for clarity) by the cutting tool 500. At least part of implant 10 should extend from first end 710 of insertion tool 700 to facilitate insertion of implant 10 into opening. The surgeon is expected to feel some resistance when inserting the partially extending portion of implant 10 or 11. However, the surgeon is expected to feel this portion slide into the opening surgically cut. During this process of inserting the surgeon can moved back and forth second end 720 of insertion tool 700 to actually cause implant 10 or 11 to enter the surgically cut opening. First end 710 will stop moving once it contacts the bony area around the opening for implant 10. During this process prongs 312 and 314 hold together the upper and lower vertebrae and maintain the shape and position of the opening for implant.

Once implant 10 has been at least partially inserted into the opening, implant 10 should be ejected from implant insertion tool 700 and more fully (preferably fully) inserted into the opening for implant. Ejecting implant 10 or 11 from insertion tool 700 and more fully inserting implant 10 or 11 into opening for implant 10 can be facilitated by impaction tool 900 which can slide through insertion tool's 700 thru opening 740 and push on implant 10 causing it to be ejected from insertion tool 700 and being more fully inserted into the opening for implant 10. FIG. 36 is a side view of an implant impaction tool 900 being inserted into the implant insertion tool 700 (insertion being schematically indicated by arrow 400) which tool 700 itself was previously inserted into guide tool 300.

The above described process can be repeated step by step for implantation of irregularly shaped implant 10 or 11 for fixation and fusion of facet joint 1230, 1231.

Irregularly shaped implant 10 can be an autograft, cadaveric allograft or FDA approved synthetic pre-made, pre-shaped cortical bone insert, implant, or graft. The procedure is envisioned to require only one implant per facet joint and two per level. Permanent fixation occurs when bone in-growth occurs into the joint itself and into the implant over time.

FIGS. 38-51 illustrate a tool 370 that can be used to remove bone tissue that has been cut with cutting tip 600 of cutter 530. If the cut bone 371 does not lodge itself in cutting tip 600, it must be removed. Tool 370 attaches to holder 550 at threaded end 570 (see FIGS. 38-39, 45-46). As a surgeon rotates handle 560 (see arrow 382, FIG. 43) of holder 550, a plurality of arms 372 of tool 370 converse on the cut bone 371 and grip it (see arrows 381, FIGS. 43,49). Arms 372 are separated by longitudinal slots 373. In order to set the tool 370 in its proper position to remove cut bone 371, a gauge 374 is employed. Gauge 374 has a cylindrical handle 376 and an implant shaped projection that corresponds generally in size and shape to the surgically cut bone to be removed. In FIGS. 42-44, a surgeon sets the position of arms 372 by placing the arms in contact with projection 375, rotating handle 550 until the arms snugly grab the implant shaped projection 375. The surgeon then reverses the rotation of handle 550 to release the projection 375 of gauge 374. The handle might be turned a half turn or a turn for example to release the projection 375 of gauge 374.

Tool 370 has an internally threaded socket 377 that is engaged with the threads 570 of holder 550. Tool 370 has a similar size and shape to cutter 530, providing flange 378 with projections 379 that fit the slots 540 of cutter sleeve 501 (see FIGS. 38-40).

Figure 45:
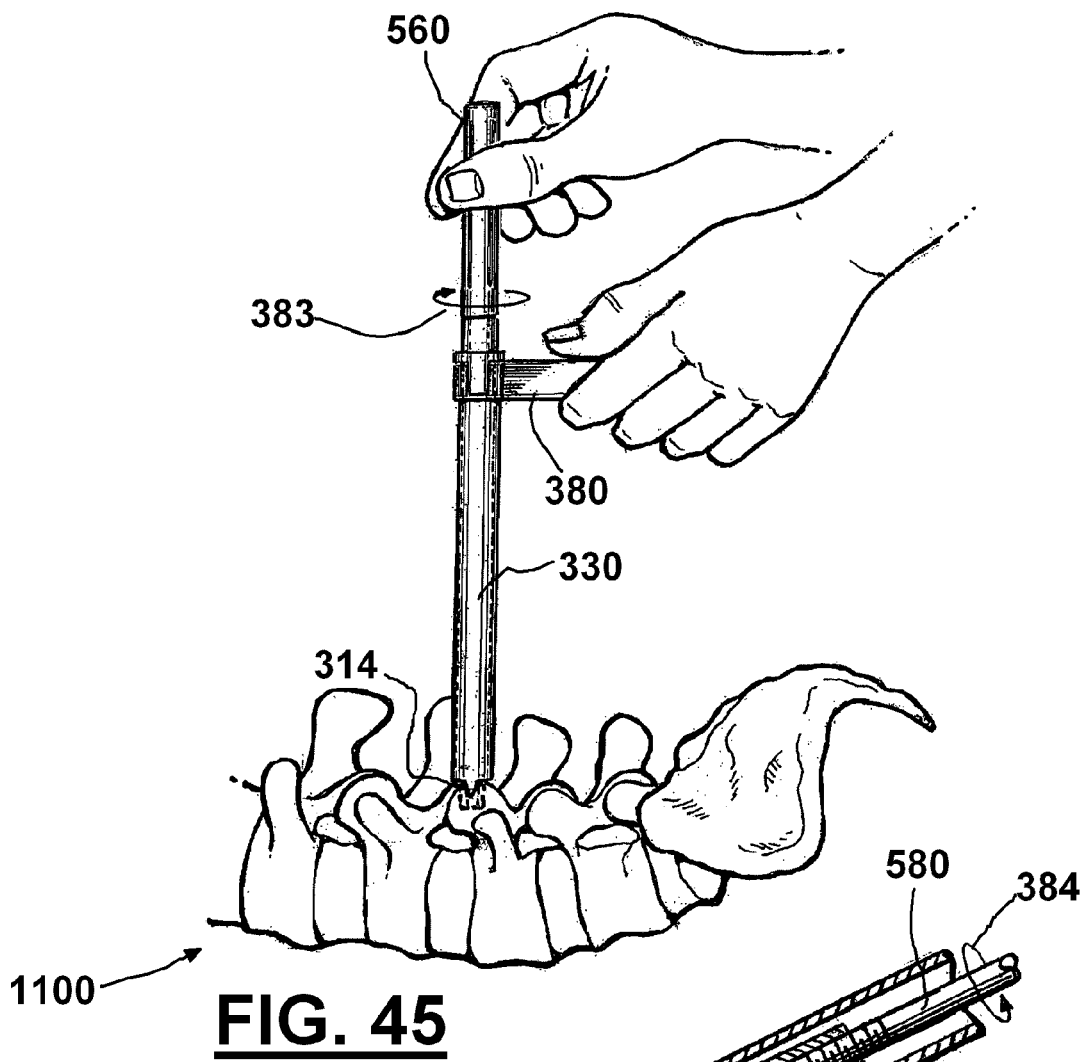
FIG. 45 is an elevation view of the preferred embodiment of the apparatus of the present invention illustrating the step of using plug or coupon removal.
Figure 46:
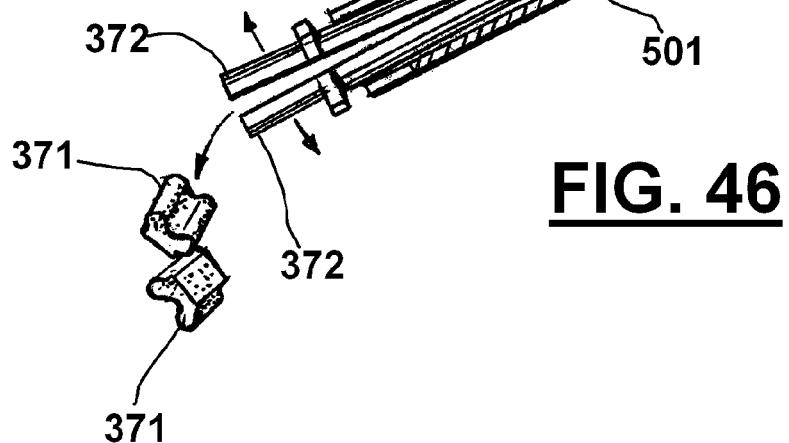
FIG. 46 is an elevation view of the preferred embodiment of the apparatus of the present invention illustrating dislodgement of the plug or coupon from the plug or coupon removal tool.

FIG. 45 shows a rotation of handle 560 (arrow 383) to grip the cut bone 371. After securing the cut bone 371, it is removed from spine 1100 and guide tool 300. Rotation of handle 560 (see arrow 384 in FIG. 46) expands arms 372 and the cut bone 371 is discharged.

FIGS. 53-68 show an alternate coupon removal assembly, method, and apparatus. In FIGS. 59, 60, 61 and 63, the coupon removal assembly is designated generally by the numeral 1400. The coupon removal assembly or plug removal assembly of FIGS. 53-68 is an alternate to the plug removing tool of FIG. 38. As with the plug removing tool of FIG. 38, the coupon removal assembly or plug removing tool 1400 (such as shown in FIGS. 53-68) could be used as part of the method and apparatus of the present invention such as in combination with the guide tool 300 during a surgical procedure that removes a coupon or plug or bone debris 371 and replaces that coupon or plug or debris 371 with an insert or implant 10, 11, 21. The coupon removal assembly 1400 can thus be used with any of the embodiments, in place of the grabbing tip plug removal tool of FIGS. 38-39.

Coupon removal assembly or plug removal tool 1400 employs a cutter 1401. The cutter 1401 includes a conically shaped coupler 1402 having an internally threaded bore 1403. The coupler 1402 can provide a frustoconically shaped outer surface 1404. The internally threaded bore 1403 is sized and shaped to form a connection with the external threads 1413 of holder 1411 as shown in FIGS. 59, 62 and 64-65. Coupon removal assembly or plug removing tool 1400 can employ the cutter sleeve 501. Sleeve 501 was also a part of the removal tool of FIGS. 38-39. Cutter sleeve 501 thus provides body 505 having first end 510 and a collar 512 at second end 520. Arms or flanges 522, 523 are spaced from body 505, and are attached to collar 512 as shown. The cutter sleeve 501 provides a longitudinally extended open ended bore 524 and slots 540 that are receptive of projections 680 of flange 670. The end 610, flange 670, projections 680 of cutter 1401 can thus be the same as for the cutter 530 of the plug removal tool shown in FIGS. 38-39 and described in related text.

Cutter 1401 can thus be similar in shape and configuration to the cutter 530 of FIG. 13. The cutter 1401 however provides conically shaped coupler 1402, internally threaded bore 1403, frustoconical surface 1404 for enabling connection to holder 1411. The internally threaded bore 1403 is configured to receive and to connect with the external threads 1413 of holder 1411 (see FIGS. 57, 59, 62-64).

Holder 1411 includes one end portion having handle 1412 to which is attached shaft 1415. The other end portion of holder 1411 provides external threads 1413 on shaft 1415. Shaft 1415 is an elongated shaft that can be tapered or frustoconically shaped (see FIGS. 57, 59). Shaft 1415 provides an open ended bore 1414 as shown in FIG. 57.

Handle 1405 (FIGS. 54, 59, 63) fits end portion 520 of cutter sleeve 501. Handle 1405 provides a socket 1406 having a smaller diameter opening 1407 and a larger diameter opening 1408 that is sized and shaped to fit end 520 of cutter sleeve 501. Handle 1405 provides appendages 1409, 1410 that can be arranged approximately one hundred eighty (180) degrees apart.

Figures 61, 62:
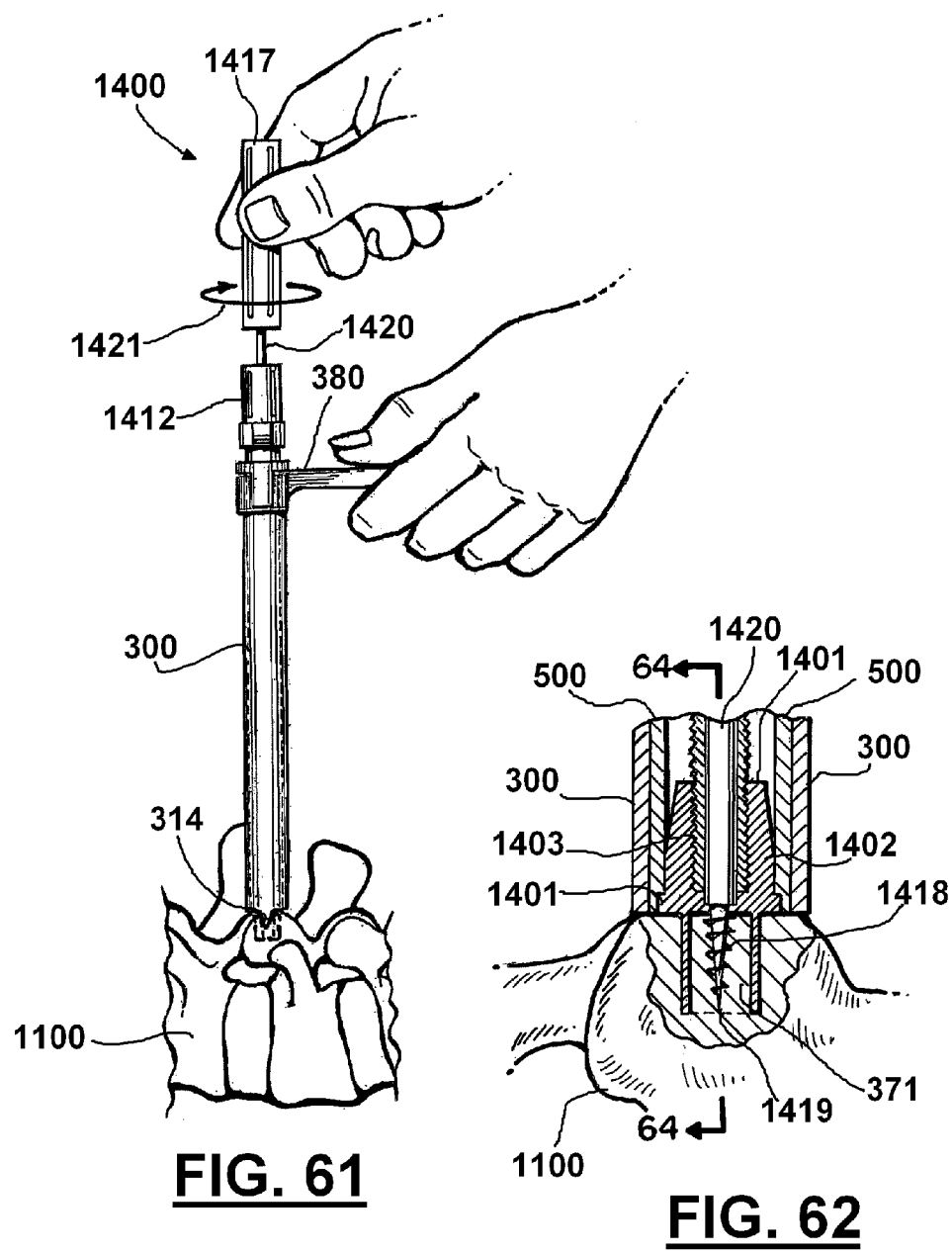
FIG. 61 is side elevation view illustrating the step of turning and screwing in the threaded wedging member into the cut or stamped plug or coupon.
FIG. 62 is a partial sectional elevation view showing the alternate plug or coupon removal assembly with the threaded wedging member screwed into the cut or stamped plug or coupon so that the two pieces of the plug or coupon are expanded against the walls of the cutting tip.

Removal tool 1416 provides a handle 1417 at one end portion and a shaft 1420 with a tip 1419 at its other end portion. An externally threaded section is provided at 1418 next to tip 1419. Shaft 1420 extends between tip 1419 and handle 1417. Shaft 1420 is sized and shaped to fit inside of bore 1414 of holder 1411 as shown in FIGS. 59, 60, 61, 62 and 63. Arrow 1421 in FIG. 61 illustrates that handle 1417 and thus removal tool 1416 can be rotated such as when engaging and imbedding the externally threaded section 1418 into a coupon or plug of bone 371 to be removed from a patient's spine 1100 at a selected facet joint.

Figure 52:
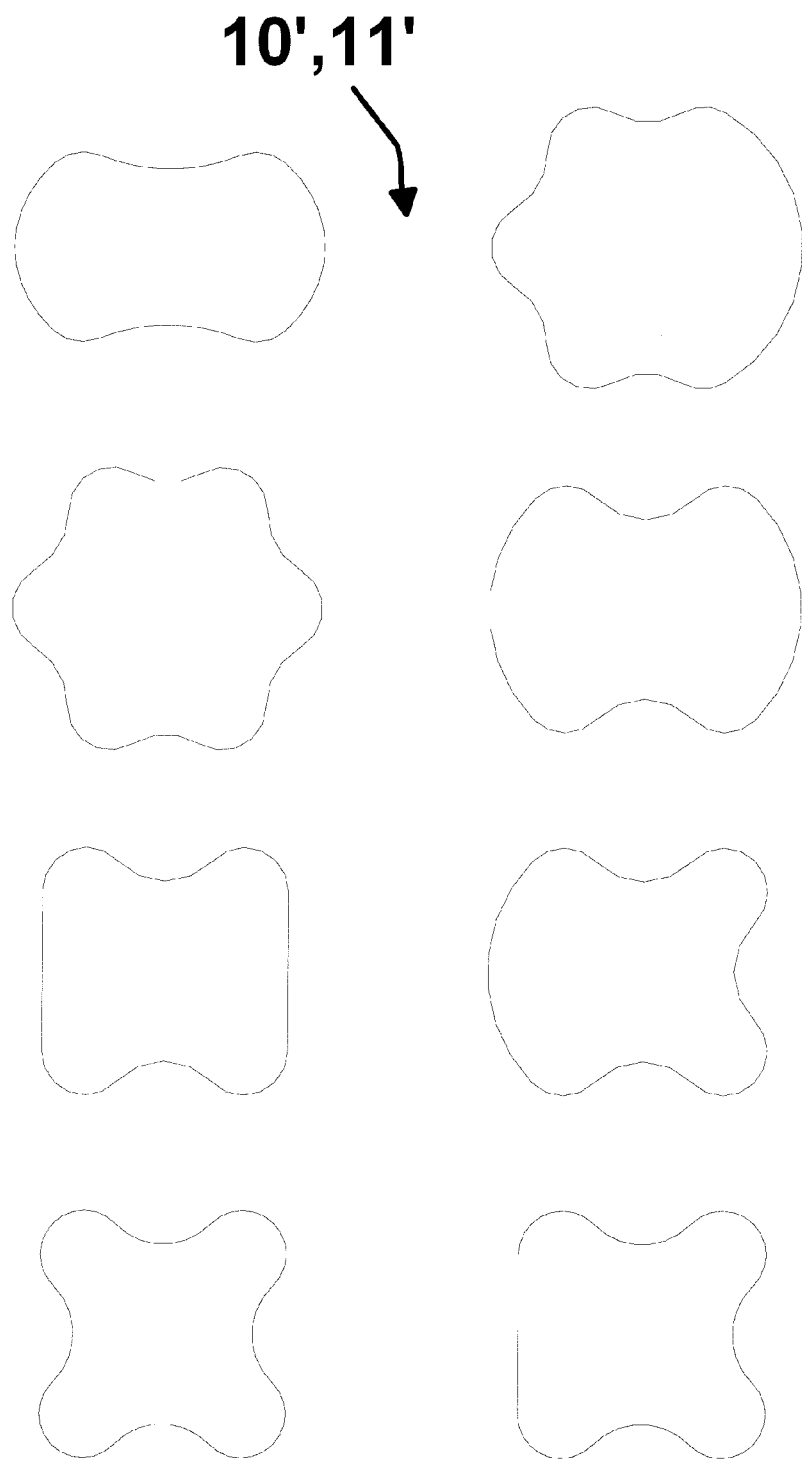
FIG. 52 includes various alternative irregular shapes for the inserts, implants, plugs, or grafts beyond an X or cross shape.
Figures 63, 64:
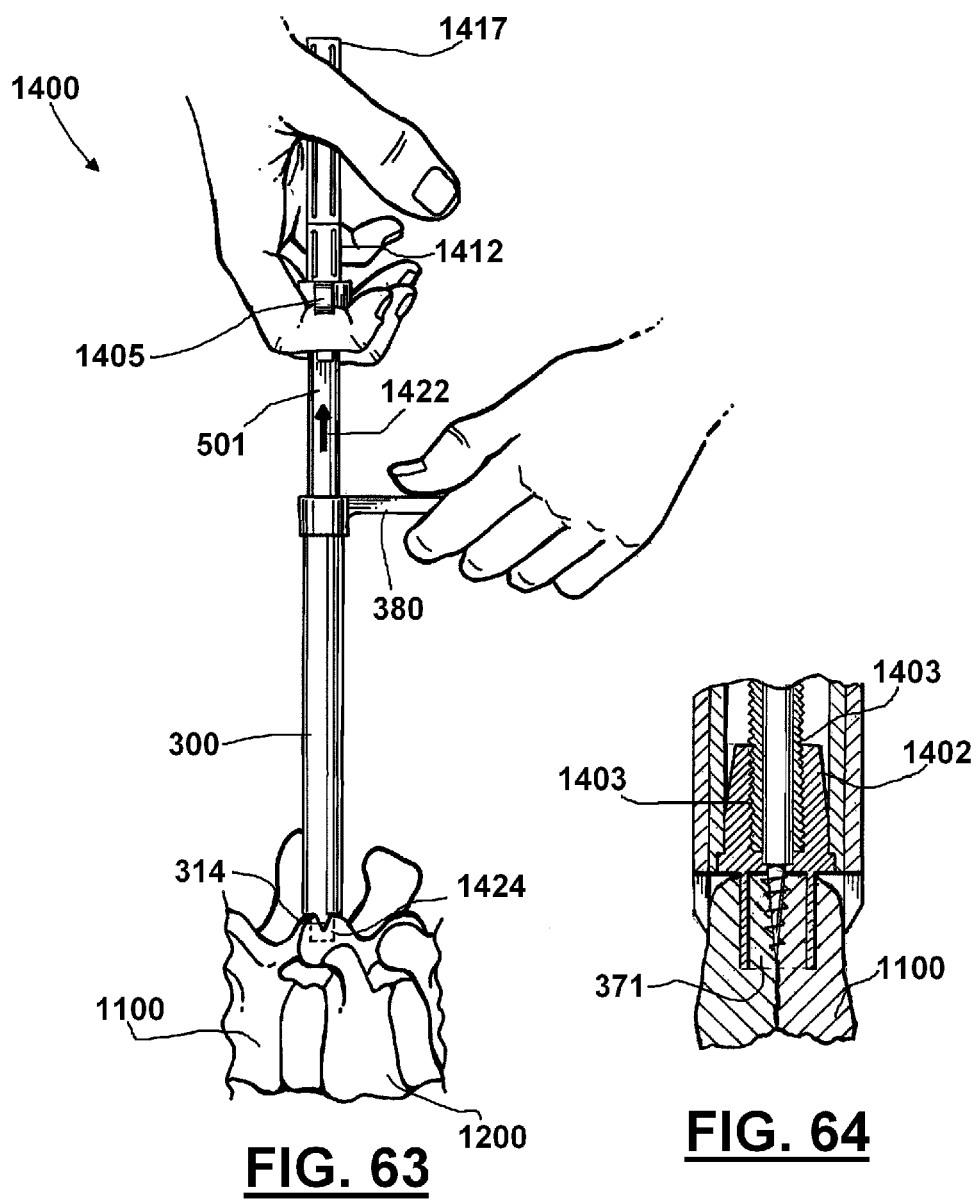
FIG. 63 is an exploded elevation view showing the alternate plug or coupon removal assembly being pulled up with the plug or coupon to form a bore or opening in the spine of a patient about the facet joint.
FIG. 64 is a sectional view taken along lines 64-64 of FIG. 62 illustrating that preferably the threaded wedging member will thread into the facet joint and then be between the two portions of the plug or coupon which causes these pieces to expand against the walls of the cutting tip along with the threads threading into each of the two pieces.

In order to remove a coupon or plug of bone 371 and thus provide a surgically cut opening or cavity 1424, a surgeon places guide tool 300 next to the patient's spine 1100 next to a selected facet joint as shown in FIG. 63 and as was shown and described with respect to the preferred embodiment of FIGS. 1-52. As shown in FIGS. 59-64, cutter sleeve 501 is placed inside of guide tool 300. Handle 1405 is placed upon end portion 520 of cutter sleeve 501. Shaft 1415 of handle 1412 is then inserted through smaller diameter opening 1407 of handle 1405 and then into the bore 540 of cutter sleeve 501. External threads 1413 of holder 1411 engage the internal threads or internally threaded bore 1403 of cutter 1401 (see FIGS. 59, 62 and 64). The cutter 1401 end 610 is then driven into the patient's spine 1100 in order to form a surgically cut opening or cavity 1424 (see FIGS. 63-65). Handle 1417 of removal tool 1416 is then rotated so that the threads 1418 engage the cut bone 371 to be removed. A surgeon then lifts the holder 1411 and removal tool 1416 upwardly by grasping the appendages 1409, 1410 of handle 1405 while supporting guide tool 300 using handle 380 as shown in FIG. 63.

Figure 65:
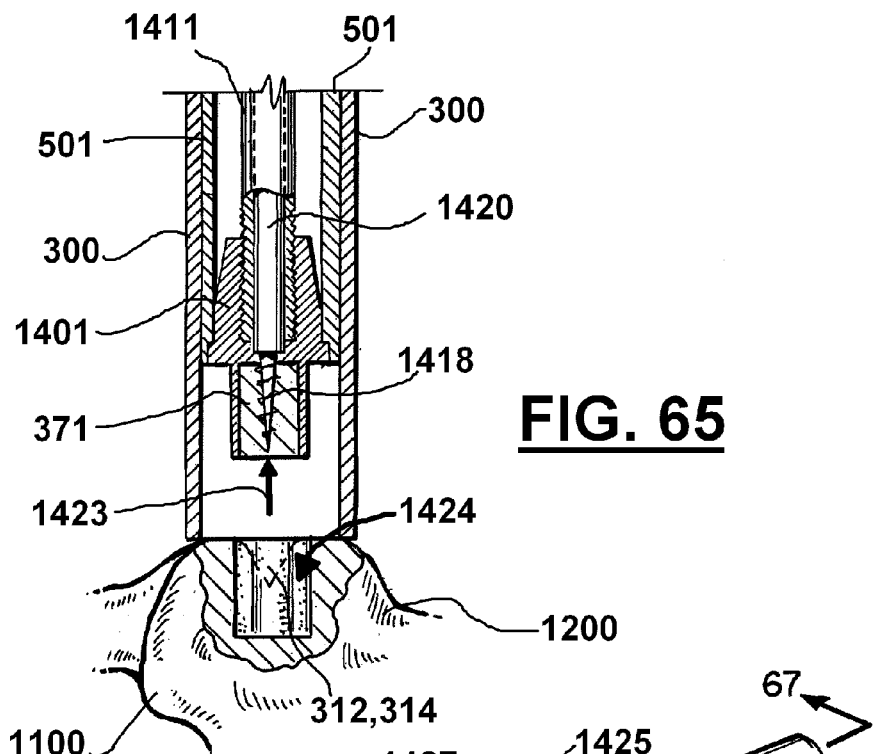
FIG. 65 is a partial sectional elevation view showing the alternate plug or coupon removal assembly being pulled up with the plug or coupon to form a bore or opening in the spine of a patient about the facet joint.

By inserting the tip 1419 and external threads 1418 at the lower end of shaft 1420 of removal tool 1416 into the spine 1100, the cut bone or coupon or plug 371 expands slightly and thus engage the first end 610 of the cutter 1401 to create a tight, a snug or an interference fit. For the cutter 1401, the first end 610 can be sized and shaped as the cutter 530 of FIGS. 10-13. Arrow 1422 illustrates this removal of the cutter sleeve 501, handle 1405, holder 1411, and removal tool 1416 together with the cut bone/coupon/plug 371. In FIG. 65, arrow 1423 schematically illustrates the removal of the cut bone/coupon/plug 371 leaving surgically cut opening or cavity 1424 in spine 1100.

Figure 66:
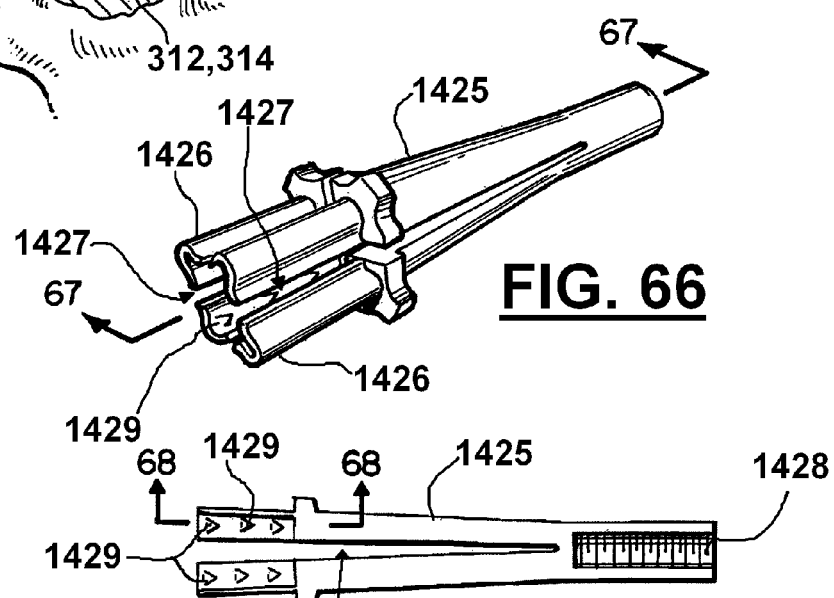
FIG. 66 is a partial perspective view showing an alternate coupon removal tool with an alternate grabbing tip with gripping spurs or burrs.
Figure 67:
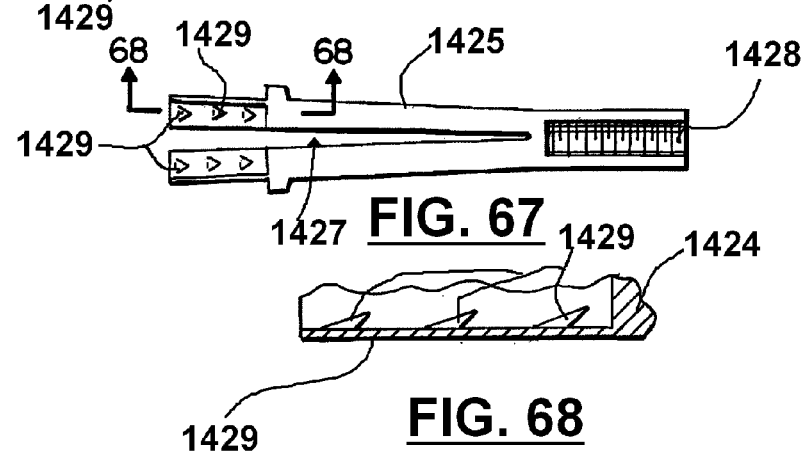
FIG. 67 is a sectional view taken along lines 67-67 of FIG. 66.
Figure 68:
FIG. 68 is a sectional view taken along lines 68-68 of FIG. 67.

In FIGS. 66-68, a bone removal tool 1425 is shown, which similar to the bone removal tool of FIGS. 38-40. Removal tool 1425 is provided with barbs 1429 on the inner surface of arms 1426 as shown in FIGS. 66-68. As with the bone removal tool 370, the bone removal tool 1425 provides arms 1426, slots 1427 separating the arms, and an internally threaded socket 1428. The use of the barbs 1429 (which are upwardly facing) helps resist slippage during removal of the coupon, plug, bone debris or or cut bone 371.

FIG. 69 is a side view of a facet joint locator 1430 having at least one longitudinal positioning line 1439. In one embodiment two longitudinal positioning lines 1439 and 1439' can be provided on opposite sides of the facet joint locator 1430 and in the same plane that contains flange/blade 1433. FIG. 70 is a sectional view of the facet joint locator 1430 taken along the lines 70-70 of FIG. 69. FIG. 71 is a perspective view of the facet joint locator 1430.

FIGS. 69-71 show facet joint locator 1430. The facet joint locator 1430 provides a proximal end portion 1431 and a distal end portion 1432. Flange 1433 is mounted at distal end portion 1432. The flange 1433 provides a tip 1434. The flange 1433 provides a tip 1434 and surfaces 1435, 1436. The surfaces 1435, 1436 can be planar surfaces that are generally parallel.

Facet joint locator 1430 has a frustoconical section 1437 and a generally cylindrically shaped section 1438. Flange 1433 attaches to frustoconical section 1437 as shown in FIGS. 69-71. An alignment mark 1439 (or multiple alignment marks 1439) can be provided on facet joint locator 1430 such as on the cylindrical section 1438 as shown in FIG. 71. The alignment mark or marks 1439 fall in a plane that is generally co-planar with one of the surfaces 1435, 1436.

Figures 72, 73:
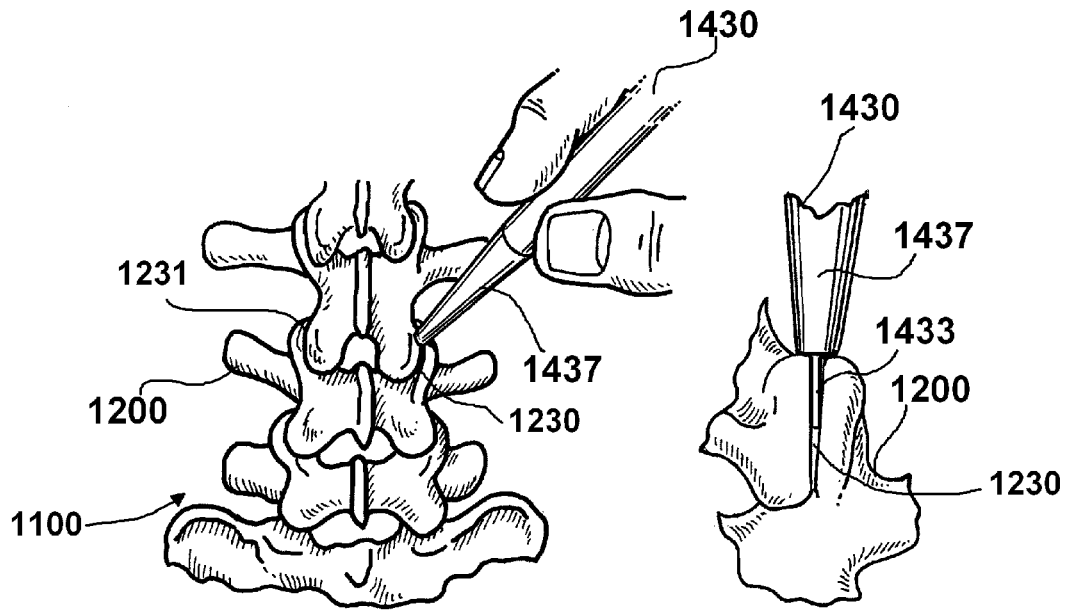
FIG. 72 is a perspective view of a step in the method and apparatus of one embodiment where the surgeon uses the facet joint locator of FIG. 69 to locate the facet joint.
FIG. 73 is a close up perspective view of the facet joint locator shown inside the facet joint.
Figures 74, 75:
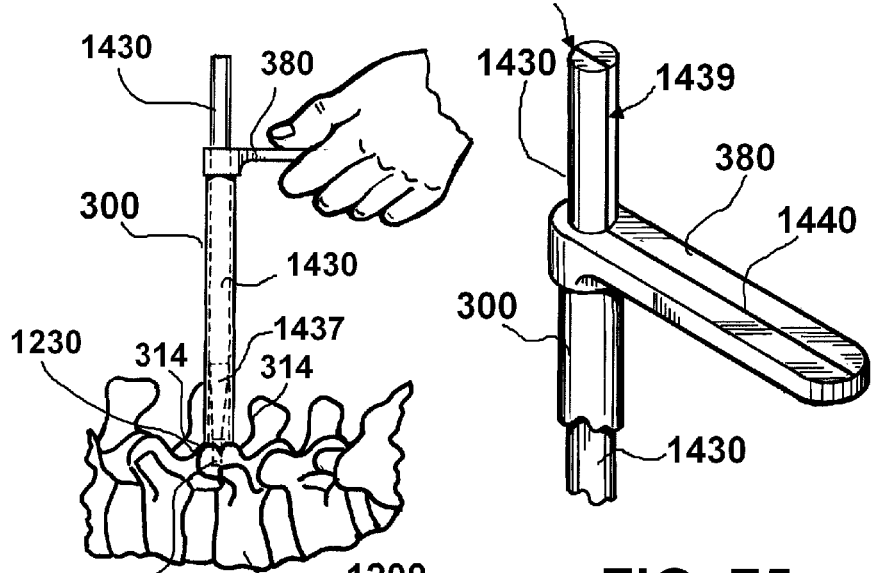
FIG. 74 is a side view of the guide tool being positioned over the facet joint locator and contacting the spine of a person over the facet joint.
FIG. 75 is a partial perspective view of the guide tool and facet joint locator where the guide tool has a positioning mark on its handle which is lined up with the positioning mark of the facet joint locator, and such lining up orients subsequent steps of the method and apparatus properly with respect to the orientation of the opening or bore in the facet joint to be fused.

FIG. 72 is a perspective view of a step in the method and apparatus of one embodiment where the surgeon uses facet joint locator 1430 to locate the facet joint in which an opening is to be made for insert, implant, plug, or graft 10,11,21. FIG. 73 is a close up perspective view of the facet joint locator 1430 shown inside the facet joint. FIG. 74 is a side view of guide tool 300 being positioned over the facet joint locator 1430 and contacting the spine 1200 of a person over the facet joint (points 314 are shown digging into the spine).

FIG. 75 is a partial perspective view of the guide tool 300 and facet joint locator 1430 where the guide tool 300 has a positioning mark 1439 which is lined up with the positioning mark 1440 in the handle 380 which alignment orients subsequent steps (cutting of opening 1424, removal of coupon or plug 371, and insertion of insert, implant, plug, or graft 10,11, 21 into opening 1424) with respect to the orientation of the opening or bore 1424 in the facet joint to be fused.

In FIGS. 72 and 73, a surgeon places the facet joint locator 1430 flange 1433 in a position that contacts the spine 1200 to locate the facet joint 1230 or 1231. FIG. 73 is a close-up perspective view of the facet joint locator 1430 shown with the flange or blade 1433 inside the facet joint 1230 or 1231. In FIG. 74, a side view of the guide tool 300 is shown being positioned over the facet joint locator 1430 and contacting the spine 1200 next to the facet joint. FIG. 75 shows that the guide tool 300 can be provided with an alignment mark 1440. The guide tool positioning mark 1440 is lined up with the alignment mark 1439 of the facet joint locator 1430. In FIG. 75, the guide tool 300 has been properly aligned with the alignment mark 1439 of the facet joint locator 1430 and thus is properly aligned with the flange or blade 1433 of the facet joint locator 1430 which engages a facet joint 1230 or 1231.

FIG. 76 is a perspective view of an insert, implant, plug, or graft 10,11,21 being placed in an alternative embodiment of the insertion tip 1500 of the method and apparatus where a portion of the insert, implant, plug, or graft 10,11,21 protrudes or extends outside of the insertion tip 1500. In this embodiment about two thirds protrudes from the insertion tip 1500.

FIG. 77 is a sectional side view of the insertion tip 1500 placing the insert, implant, plug, or graft 10,11,21 into the opening or bore 1424 previously made around the facet joint (1230 or 1231) of a person's spine 1200 where the orientation of the insert, implant, plug, or graft 10,11,21 is maintained with the opening or bore 1424 based on the orientation of the original facet joint locator 1430 shown in FIG. 75.

FIG. 76 is a perspective view of an insert, implant or plug such as implant 10, 11, 21 being attached to an alternative insertion tip 1500. Insertion tip 1500 can have first end 1520 and second end 1530. First end 1520 can have a threaded internal bore which is connected with opening 1540 of second end 1530. Tip 1500 can have an externally tapered section 1510 and include a plurality of slots on the second end 1530. Tip 1500 can also include a plurality of alignment projections or tips 1560 which cooperate with the plurality of slots 540 of tool 500 in order to orient the alignment of opening 1540 with the cut or opening 1424 made previously in the spine 1200 about the facet joint.

Opening 1540 can correspond to the respective shape of insert, implant, or plug 10,11,21 and include a shoulder 1550 restricting the longitudinal depth to which insert, implant, or plug 10,11,21 can be inserted into opening 1540. Tip 1500 can be properly aligned with respect to tool 500. Because tool 500 is aligned with respect to guide tool 300 (by arms 522 and 523 limiting movement with respect to handle 380 of guide tool 300), the opening 1550 (and implant, insert, or plug 10,11,21) will be aligned with opening 1424 in spine 1200.

If the shape of the insert, implant, or plug 10,11,21 is symmetrical then the relative positioning of the alignment projections or tips 1560 are not that important as falling within any slot 540 will align the shape of opening 1540 with the cut or opening 1424 in spine 1200. If the shape of insert, implant, or plug 10,11,21 is not symmetrical then the plurality of slots 540 can be made to respectively fit only a certain number of the plurality of alignment tips or projections 1560. For example, these two sets (540 and 1560) can be numbered respectively to provide the proper alignment. Alternatively, they can be different shapes or sizes to force a particular alignment between tip 1500 and tool 500. Similarly, the alignment of cutting tip 610 (with its alignment prongs or tips 680) and grabbing tip 1425 (with its plurality of alignment prongs or tips) can be obtained. In this manner, from the original cutting of the opening 1424, removal of the coupon or plug 371, and insertion of the insert, implant, or plug 10,11,21 the proper orientation can be made with respect to the facet joint, opening to be made, and insert, implant, or plug to be inserted for fusion of the facet joint.

Figure 59:
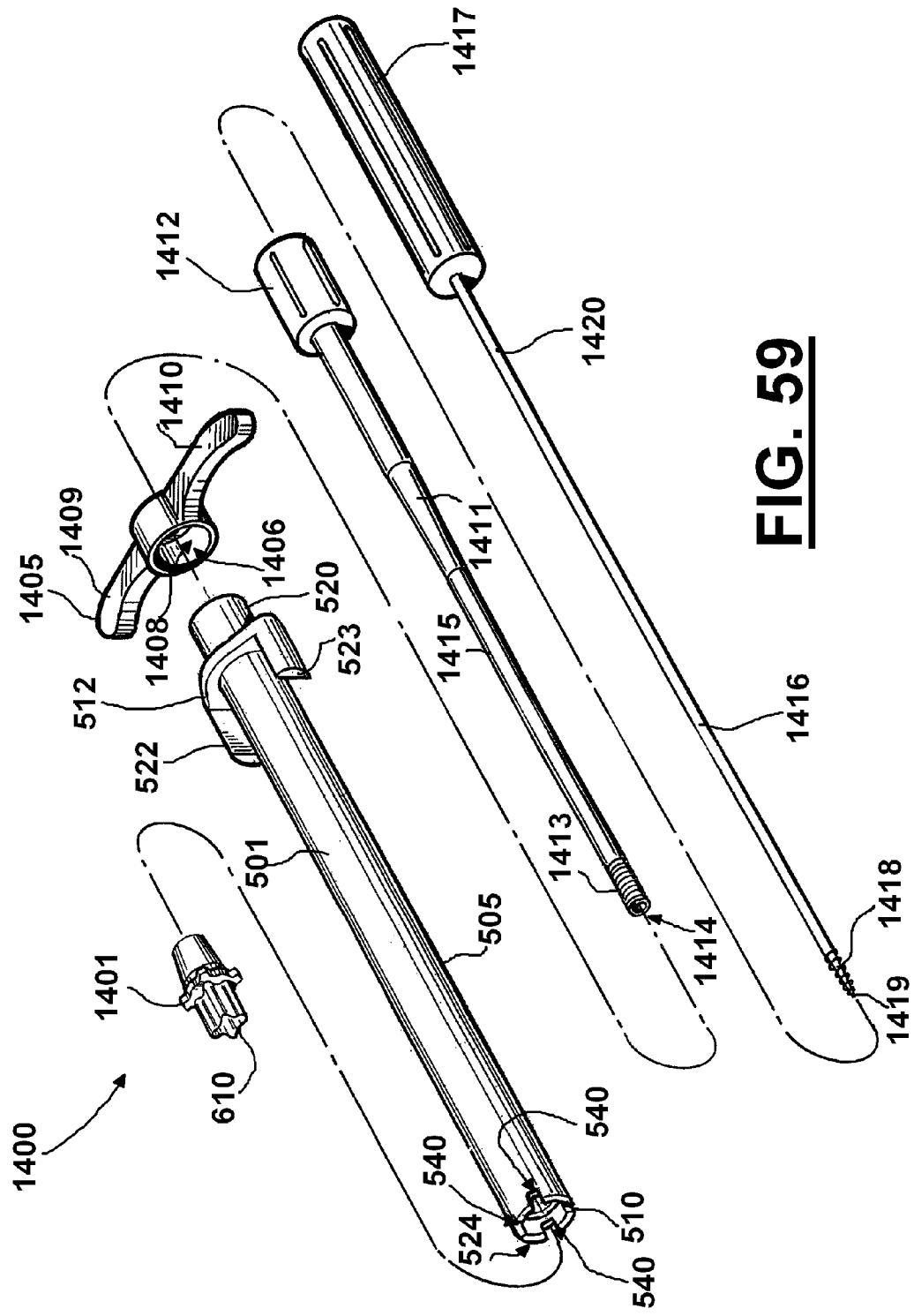
FIG. 59 is an exploded perspective view illustrating the steps of assembling the alternate plug or coupon removal tool.
Figure 60:
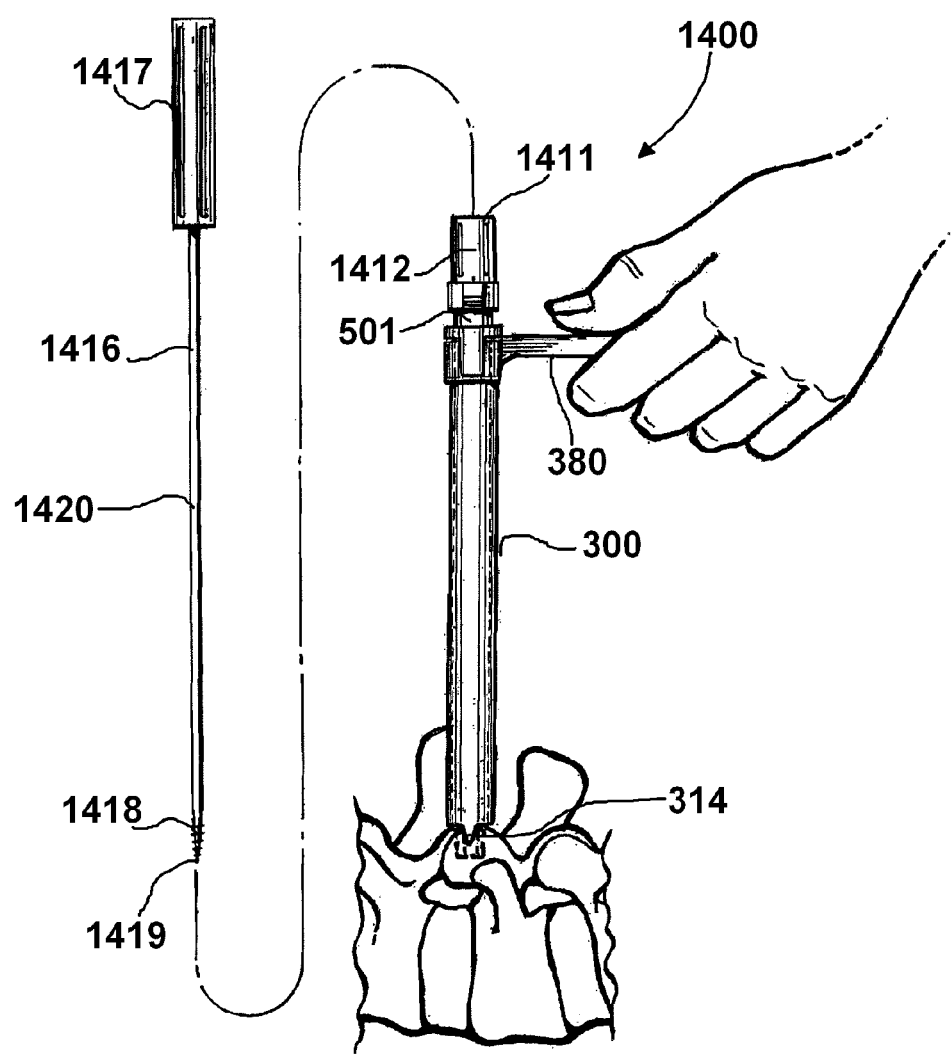
FIG. 60 is an exploded elevation view illustrating the step of inserting the threaded wedging member into the alternate coupon tool after the tool was used to cut the bore or opening in a patient's spine about the facet joint.

Alternative insertion tip 1500 allows the surgeon to control the amount of force the tip 1500 places on insert, implant, or plug 10,11,21 while being held in opening 1540. FIG. 77 shows tip 1500 threadably connected to holder 1411. Tapered section 1510 of tip 1500 is in contact with internally tapered portion of tool 500. Plurality of alignment tips or prongs 1560 are shown located in alignment slots 540 of tool 500. If handle 1411 is turned in the direction of arrow 1514 tip 1500 will move in the opposite direction of arrow 1516 which will cause the second end 1530 to be squeezed inwardly as schematically indicated by arrows 1512 in FIG. 76. Handle 1410 will rest on second end 520 of tool 500 (see FIG. 59 showing connection to cutting tip 610 but connection with insertion tip 1500 will be substantially similar). As squeezed in the direction of arrows 1512 greater grabbing force is placed on insert, implant, or plug 10,11,21 to prevent it from falling out of tip 1500 and also maintain proper longitudinal alignment between insert, implant, or plug and the centerline of opening 1424 from the time tool 500 (with tip 1500 and insert, implant, or plug 10,11,21) is inserted into guide tool 300 and insert, implant, or plug is inserted into opening 1424.

Insert, implant, or plug 10,11,21 protrudes from tip 300 because it is believed that a protruding condition facilitates placement of insert, implant, or plug into opening 1424. Shoulder 1560 limits or restricts the amount of insertion of insert, implant, or plug 10,11,21. In different embodiments the protrusion is about 1/16, 1/8, 1/7, 1/6, 1/5, 1/4, 1/3, 1/2, 2/3, or 3/4 of the insert's, implant's, or plug's length. In various embodiments the protrusion is within a range of between about any two of the above specified amounts.

In FIGS. 77 and 78, insertion tip 1500 could thus provide an internally threaded socket 1521 having internal threads that are sized and shaped to engage the external threads 1413 of holder 1411. In FIGS. 77 and 78, there is provided a sectional side view of the insertion tip 1500 placing the insert, implant or plug 10, 11, 21 into the surgically formed opening 1424 in facet joint 1230 or 1231 that was formed previously such as be using cutter 1401). A surgically formed opening 1424 can be cut or stamped in the patient's spine 1200 at the facet joint as aforedescribed. The orientation of the insert, implant or plug 10, 11, 21 is maintained based upon the orientation of the original facet joint locator tool 1430. In FIG. 78, the insertion rod or impaction tool 900 of FIG. 23 is used to fully push the insert, implant, plug or graft 10, 11, 21 into the surgically formed opening 1424 at the facet joint 1230 or 1231.

Surgical Method

In one embodiment the method and apparatus includes an allograft designed to fuse the facet joint. The facet joint can be identified either via an open approach (traditional laminectomy exposure) or via a percutaneous approach with stab incisions on either side of the spinous process at the appropriate level. In this approach you will need to use fluoroscopy to localize the appropriate joint and location.

An implant opening can be made via a bone stamper, cutter (or die) by setting the cutter or (die) on the dorsum of the facet joint and gently impacting until being flush on the joint surface. The position of the opening (Cartesian and/or rotational) can be determined by a positioning selector and maintained via a guide in which all tools are positionally determined. The cutter or stamper can be withdrawn after partial closure of the terminus of the stamper. The joint material (cartilage and bone primarily) with be withdrawn as this device exits the joint.

Stamping an opening is advantageous to other devices which drill or "grind" the tissue and/or bone. This can have adverse effects on arthrodesis. The cutter or stamper can be slightly undersized allowing for an ultimate press fit of a graft into the implant opening made by the stamper. The implant can then be placed into the guide tool which correctly positions the implant for insertion into the opening. The implant can then be impacted gently into the opening created in the facet joint until it seats flush with the opening. All tools can then be withdrawn and the patient closed.

In one embodiment the irregularly shaped implant can lock the two "hands" (or upper and lower halves) of the facet joint together. This locking will then lead to accelerated fusion of the joint and decrease in the generation of pain.

The following is a list of reference numerals:

LIST FOR REFERENCE NUMERALS

| (Part No.) Reference Numeral | (Description) Description |
|---|---|
| 10 | insert/implant |
| 11 | insert/implant |
| 20 | first side |
| 21 | implant |
| 22 | ridge |
| 30 | second side |
| 40 | depth or height |
| 42 | protruding section |
| 50 | prong or arm |
| 51 | tip |
| 52 | taper from first side to second side |
| 54 | valley between prongs or arms |
| 60 | prong or arm |
| 61 | tip |
| 62 | taper from first side to second side |
| 64 | valley between prongs or arms |
| 70 | prong or arm |
| 71 | tip |
| 72 | taper from first side to second side |
| 74 | valley between prongs or arms |
| 80 | prong or arm |
| 81 | tip |
| 82 | taper from first side to second side |
| 84 | valley between prongs or arms |
| 90 | center |
| 92 | longitudinal axis |
| 100 | line |
| 120 | line |
| 300 | guide tool |
| 310 | first end |
| 312 | insertion prong |
| 314 | insertion prong |
| 320 | second end |
| 330 | body |
| 340 | thru opening |
| 360 | rounded wall of thru opening |
| 370 | bone removal tool |
| 371 | cut bone/coupon/plug |
| 372 | arm |
| 373 | slot |
| 374 | gauge |
| 375 | implant shaped projection |
| 376 | cylindrical handle |
| 377 | internally threaded socket |
| 378 | flange |
| 379 | projection |
| 380 | handle |

-continued

| (Part No.) Reference Numeral | (Description) Description |
|---|---|
| 381 | arrow |
| 382 | arrow |
| 383 | arrow |
| 384 | arrow |
| 385 | surgically cut opening/cavity |
| 390 | arrows |
| 392 | arrows |
| 394 | mallet |
| 396 | arrow |
| 500 | bone cutter/bone cutting tool assembly |
| 501 | cutter sleeve |
| 505 | body |
| 510 | first end |
| 512 | collar |
| 520 | second end |
| 522 | arm/flange |
| 523 | arm/flange |
| 524 | bore |
| 530 | cutter |
| 540 | slot |
| 550 | holder |
| 560 | handle |
| 570 | threads |
| 580 | shaft |
| 600 | cutting tip |
| 610 | first end |
| 620 | second end |
| 622 | threaded area |
| 640 | depth of cutting tip |
| 652 | prong or arm |
| 653 | valley between prongs or arms |
| 656 | prong or arm |
| 657 | valley between prongs or arms |
| 660 | prong or arm |
| 661 | valley between prongs or arms |
| 664 | prong or arm |
| 665 | valley between prongs or arms |
| 670 | flange |
| 680 | projection |
| 700 | tool for holding and inserting implant or insert |
| 710 | first end |
| 712 | plurality of cutouts/slots |
| 714 | depth of the plurality of cutouts |
| 720 | second end |
| 730 | body |
| 740 | thru opening in body/bore |
| 800 | opening for receiving implant or insert |
| 810 | depth of opening |
| 852 | prong or arm |
| 856 | prong or arm |
| 860 | prong or arm |
| 864 | prong or arm |
| 900 | impaction tool |
| 910 | first end |
| 920 | second end |
| 922 | handle |
| 930 | body |
| 1100 | spinal column |
| 1200 | vertebrae |
| 1210 | upper portion of facet joint for vertebra |
| 1211 | upper portion of facet joint for vertebra |
| 1220 | lower portion of facet joint for vertebra |
| 1221 | lower portion of facet joint for vertebra |
| 1230 | facet joint |
| 1231 | facet joint |
| 1232 | plane of facet joint |
| 1233 | plane of facet joint |
| 1300 | vertebra |
| 1310 | upper portion of facet joint for vertebra |
| 1311 | upper portion of facet joint for vertebra |
| 1320 | lower portion of facet joint for vertebra |
| 1321 | lower portion of facet joint for vertebra |
| 1400 | coupon removal assembly |
| 1401 | cutter |
| 1402 | conically shaped coupler |

-continued

| (Part No.) Reference Numeral | (Description) Description |
|---|---|
| 1403 | internally threaded bore |
| 1404 | frustoconical surface |
| 1405 | handle |
| 1406 | socket |
| 1407 | smaller diameter opening |
| 1408 | larger diameter opening |
| 1409 | appendage |
| 1410 | appendage |
| 1411 | holder |
| 1412 | handle |
| 1413 | external threads |
| 1414 | bore |
| 1415 | shaft |
| 1416 | removal tool |
| 1417 | handle |
| 1418 | externally threaded section |
| 1419 | tip |
| 1420 | shaft |
| 1421 | arrow |
| 1422 | arrow |
| 1423 | arrow |
| 1424 | surgically cut opening/cavity |
| 1425 | bone removal tool |
| 1426 | arm |
| 1427 | slot |
| 1428 | internally threaded socket |
| 1429 | barb |
| 1430 | positioning selector tool (e.g., facet joint locator) |
| 1431 | proximal end |
| 1432 | distal end |
| 1433 | flange/blade |
| 1434 | tip |
| 1435 | surface |
| 1436 | surface |
| 1437 | frustoconical section |
| 1438 | cylindrical section |
| 1439 | alignment mark |
| 1440 | alignment mark |
| 1500 | insertion tip |
| 1510 | tapered portion |
| 1512 | arrows |
| 1514 | arrow |
| 1520 | first end |
| 1521 | longitudinal bore or opening |
| 1522 | threads |
| 1530 | second end |
| 1540 | opening |
| 1550 | shoulder |
| 1560 | plurality of alignment tips |

All measurements disclosed herein are at standard temperature and pressure, at sea level on Earth, unless indicated otherwise. All materials used or intended to be used in a human being are biocompatible, unless indicated otherwise.

It will be understood that each of the elements described above, or two or more together may also find a useful application in other types of methods differing from the type described above. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention set forth in the appended claims. The foregoing embodiments are presented by way of example only; the scope of the present invention is to be limited only by the following claims.

The invention claimed is:

1. A method of mounting an implant in a facet joint C1-C2 and L5-S1, the method comprising the steps of:
   (a) cutting an arthroscopic type portal in the tissue of a patient outside a diseased or damaged facet joint;
   (b) using a positioning selection tool to select an orientation of a plug to be implanted, the selected orientation including a plurality of prongs defining an orientation of the plug to be implanted;
   (c) placing an implantation guide in operative connection with the positioning selection tool;
   (d) while maintaining at least two distinct prongs of the selected orientation removing the positioning selection tool from operative connection with the implantation guide;
   (e) placing a cutting tool in operative connection with the implantation guide, and using operative connection between the cutting tool and implantation guide to form a shaped hole between two opposed bones forming the facet joint, the shaped hole having at least the two distinct prongs of orientation specified in step "d"; and
   (f) inserting a preshaped plug into the hole, the plug having a shape substantially the same as the hole.

2. The method of claim 1, wherein in step "f" the plug comprises:
   (i) a substantially solid body having a longitudinal axis;
   (ii) a plurality of opposed arms, the arms being symmetrically disposed around the longitudinal axis; and
   (iii) the body being formed from a material selected from the group consisting of synthetic cortical bone, a harvested synthetic cortical and compacted iliac crest graft and a cadaveric allograft.

3. The method of claim 2, wherein there are four arms.

4. The method of claim 3, wherein the four arms form an "X".

5. The method of claim 2, wherein the arms include tips which are rounded.

6. The method of claim 5, wherein between each pair of arms is a valley which valley is rounded.

7. The method of claim 2 wherein the body is formed from synthetic cortical bone.

8. The method of claim 2 wherein the body is formed from a harvested and compacted iliac crest graft.

9. The method of claim 2 wherein the body is formed from a cadaveric allograft.

* * * * *